United States Patent
Ding et al.

(10) Patent No.: US 12,325,862 B2
(45) Date of Patent: Jun. 10, 2025

(54) COMPOSITIONS AND METHODS FOR TRANSGENIC CROPS RESISTANT TO THAXTOMINS

(71) Applicant: University of Florida Research Foundation, Inc., Gainesville, FL (US)

(72) Inventors: Yousong Ding, Gainesville, FL (US); Guangde Jiang, Gainesville, FL (US)

(73) Assignee: **UNIVERSITY OF FLORIDA RESEARCH F

COMPOSITIONS AND METHODS FOR TRANSGENIC CROPS RESISTANT TO THAXTOMINS

RELATED APPLICATIONS

This application is the 35 U.S.C. § 371 national stage of PCT application having serial number PCT/US2020/064325, filed on Dec. 10, 2020 having the title COMPOSITIONS AND METHODS FOR TRANSGENIC CROPS RESISTANT TO THAXTOMINS, which claims the benefit of U.S. Provisional Application Ser. No. 62/946,069, filed Dec. 10, 2019, both of which are incorporated herein by reference in their entirety.

SEQUENCE LISTING

The instant application contains a Sequence Listing which has been submitted electronically as a text file and is hereby incorporated by reference in its entirety. Said text file, created on Dec. 8, 2020, is named 222107-2630_ST25.txt and is 5,093 bytes in size.

FIELD

The present disclosure relates to compositions and methods for transgenic crops resistant to thaxtomins.

BACKGROUND

Pathogens and pests are estimated to lead to 17.2%-30% yield losses of various crops globally. Accordingly, synthetic pesticides, fungicides, and antimicrobials have been developed to fight against pathogens and pests. These chemicals have achieved tremendous successes but have also caused lasting issues, e.g., emerging resistance, environment pollution, and the killing of beneficial insects. In the past decades, several new strategies have emerged to address the above-mentioned issues. For example, chemicals that are originated from natural products have increasingly been developed for crop protection, as they can offer new mechanisms of action, can act on new targets, and have minimal to no environmental impacts. Genetic engineering of crops to introduce new traits for crop protection has become another successful strategy in recent years. For example, Roundup Ready® crops are resistant to Roundup® (glyphosate), which is the most widely used herbicide.

*Streptomyces* scabies and several other *Streptomyces* species are gram positive, filamentous bacterial plant pathogens that induce diseases to broadleaf crops (e.g., potato, radish, and onion). Among these diseases, potato common scab is the most severe and widespread and incurs enormous economic losses to farmers. Almost all known plant pathogenic *Streptomyces* strains produce thaxtomins. Purified thaxtomins alone are able to induce common scab disease symptoms and are known virulent factors of plant pathogens. Importantly, thaxtomins demonstrate a novel mechanism of action, inhibiting cellulose biosynthesis at the nM range and have been developed as bioherbicides for weed control. Various methods have been explored to cure potato scab disease caused by thaxtomin-producing pathogenic *Streptomyces* strains. A somatic cell selection approach has been developed using thaxtomin A as a positive selection agent to obtain *Solanum tuberosum* variants with significantly improved resistance to common scab disease but has met with limited success. Furthermore, the synthetic compound 2,4-dichlophenoxyacetic acid has been used to fight the disease but its adverse effects to human health make it problematic. In recent years, many biocontrol strategies have been developed to control common scab of potato by using microbial species including *Pseudomonas* sp. LBUM 22322-24, *Bacillus altitudinis* strain AMCC 10130425, *Bacillus amyloliquefaciens* BAC0326-29, *Streptomyces* A1RT30, and *Streptomyces violaceusniger* AC12AB31. However, these biocontrol strategies require extra efforts to maintain strain balance. Therefore, there is a lasting need for new agents and strategies for controlling potato common scab.

Several studies have demonstrated that the nitro group of thaxtomins is essential to their virulent and herbicidal activities. The transformation of the nitro group of thaxtomins thus stands out as a potential promising strategy for controlling potato common disease. Although chemical reduction of the nitro group of thaxtomins into amine group is possible, the chemical reaction is not compatible with living organisms such as crops. In this regard, biological approaches, specifically enzymatic reduction of the nitro group, are more environmentally sound. More importantly, genetic engineering of crops with the corresponding genes has a promise to confer resistance to thaxtomins as well as thaxtomin-producing plant pathogens in the resulting crops.

Flavin mononucleotide-dependent nitroreductases form an enzyme superfamily containing more than 24,000 sequences from all domains of life. These enzymes catalyze a diverse range of reactions and some may initiate the catabolism of nitroaromatic compounds. For example, several previous studies have shown that the nitroreductase NfsB from different microbial species can reduce the nitro group of many synthetic chemicals and natural products. Very recently, the nitroreductase NfsB from *Haemophilus influenzae* was shown to catalyze the reduction of the nitro group of a series of nitro-containing chemicals. Furthermore, previous studies have shown that some bacterial and fungal species may express nitroreductases to degrade thaxtomins, although specific enzymes have not been identified. All of these studies indicated that nitroreductases can provide a way to reduce the nitro group of thaxtomins, thereby disarming thaxtomins' virulent and herbicidal activity.

Despite advances in research relating nitroreductase proteins, there is still a scarcity of strategies for combating diseases of commercially-important crops caused by thaxtomins. Furthermore, although thaxtomins are effective, naturally-occurring herbicides, they cannot currently be used as such due to off-target damage to crop plants. It would be desirable to produce thaxtomin-resistant plants in order to enable use of thaxtomins as herbicides. These needs and other needs are satisfied by the present disclosure.

SUMMARY

In accordance with the purpose(s) of the present disclosure, as embodied and broadly described herein, the present disclosure, in one aspect, relates to compositions comprising nitroreductase enzymes; plants, plant calluses, plant seeds, and vegetables incorporating genes expressing nitroreductase enzymes; methods for stably and operably incorporating genes expressing nitroreductase enzymes into plants and plant tissues; wherein the nitroreductase enzymes are capable of reducing nitro groups on phytotoxic and/or otherwise harmful compounds such as, for example, thaxtomins, wherein the thaxtomins are secreted by plant pathogenic bacteria and/or exogenously applied as an agricultural composition such as an herbicide, and wherein reducing the nitro groups renders the thaxtomins non-damaging or reduces the level of damage from the thaxtomins to the plants expressing the nitroreductase enzymes.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the present disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A. HPLC spectra of the transformations of thaxtomins A to D. The chemicals were detected at both 280 nm and 380 nm (specific to the nitro group). FIG. 3B. LC-MS detection of the $[M+1]^+$ peak of compound 5, which is indicated in the box.

FIG. 4A: $^1$H NMR (600 MHZ, $CD_3OD$); FIG. 4B: $^{13}$C NMR (150 MHz, $CD_3OD$); FIG. 4C: COSY; FIG. 4D: HSQC; FIG. 4E: HMBC.

Figure 1:
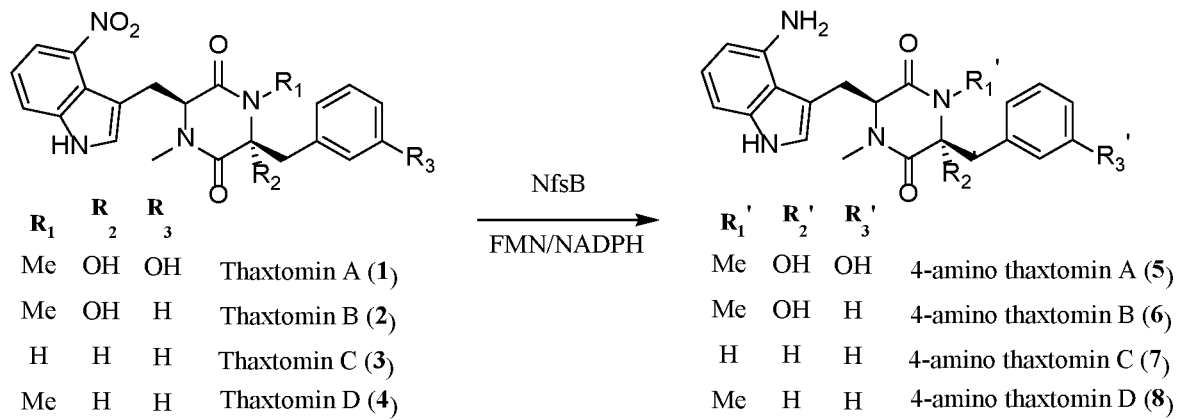
FIG. 1 shows enzymatic transformation of thaxtomins into 4-amino thaxtomins by the nitroreductase NfsB.

Additional advantages of the present disclosure will be set forth in part in the description which follows, and in part will be obvious from the description, or can be learned by practice of the present disclosure. The advantages of the present disclosure will be realized and attained by means of the elements and combinations particularly pointed out in the appended claims. It is to be understood that both the foregoing general description and the following detailed description are exemplary and explanatory only and are not restrictive of the present disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the present disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a thaxtomin," "a crop plant," or "a nitroreductase enzyme," including, but not limited to, combinations of two or more such thaxtomins, crop plants, or nitroreductase enzymes, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the present disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of as herbicidal composition refers to an amount that is sufficient to achieve the desired control of target weeds. The specific level in terms of grams per acre in a composition required as an effective amount will depend upon a variety of factors including the amount and type of level of weed growth, stage of weed growth, and stage of crop plant growth.

As used herein, the terms "optional" or "optionally" means that the subsequently described event or circumstance can or cannot occur, and that the description includes instances where said event or circumstance occurs and instances where it does not.

As used herein, "phytotoxic" refers to a deleterious effect of a compound on plant growth. In one aspect, application of a phytotoxic compound can kill all or a portion of a plant, can slow or stunt a plant's growth, can damage a plant organ such as a leaf, stem, root, fruit, flower, or the like, can inhibit seedling growth, or a combination thereof.

"Transgenic" as used herein refers to an organism that contains genes or genetic material from an unrelated organism ("exogenous DNA"). In a further aspect, the exogenous DNA in a transgenic organism can be artificially introduced in a laboratory setting. In a still further aspect, the exogenous DNA in a transgenic organism can be introduced into the organism's cells as part of a plasmid, or can be introduced into the organism's genome or the genome of a plastid (e.g., chloroplast) or mitochondrion using any technique known in the art including, but not limited to use of a biolistic device or a genome editing technique such as, for example, use of an engineered nuclease (i.e., meganucleases, zinc finger nucleases, transcription activator-like effector-based nucleases, and/or CRISPR/Cas9). In one aspect, exogenous DNA is introduced into plant callus from which plants incorporating the exogenous DNA can later be grown.

A "recombinant organism" is an organism containing an artificially-induced mutation distinguishing it from wild-type organisms. In one aspect, a recombinant organism can incorporate a gene from an unrelated species that has been introduced by genetic modification or genome editing techniques, or can incorporate a plasmid that has been so engineered. In a further aspect, disclosed herein are recombinant plants incorporating nitroreductase enzymes.

As used herein, a "primer" is a short nucleic acid sequence that provides a starting point for DNA synthesis (for example, for use in the polymerase chain reaction). Primers useful herein can be synthesized by any technique known in the art including solid-phase synthesis using phosphoramidite chemistry. In one aspect, SEQ ID NO: 2 and SEQ ID NO: 3 represent primers useful for scaling-up synthesis of one nitroreductase gene useful in the processes disclosed herein. Ideal primers have sequence overlap with the DNA that is desired to be inserted into the cell but do not form secondary or tertiary structures (i.e., hairpins, G-quadruplexes, or the like).

An "expression vector" is typically a plasmid or virus designed to introduce one or more target genes into a cell. In one aspect, an expression vector contains regulatory sequences (i.e., enhancers, promoters, and the like) that interact with the host cell's protein synthesis machinery to produce the proteins encoded by the target genes.

As used herein, a "plasmid" is a DNA molecule within a cell that is not part of the cell's chromosomal DNA. Plasmids are typically circular and double-stranded and are most commonly found in bacteria but can, in some cases, be present in archaea or eukaryotes (i.e., plasmids in yeasts or Ti-plasmids for introducing genes into plants).

"Transformation" as used herein is genetic alteration of a cell by uptake of DNA from its surroundings. In some aspects, transformation is accomplished artificially. In one aspect, transformed cells can express proteins encoded by the exogenous DNA. In some aspects, transformation as it relates to eukaryotic cells (such as, for example, plants) may be referred to as "transfection."

A "restriction enzyme" (also known as a restriction endonuclease) is an enzyme that cleaves double-stranded DNA at a specific recognition site. Restriction enzymes are native to bacteria and archaea and many can be purchased commercially for use in genetic engineering applications. Restriction enzymes may cut such that there are overhanging or "sticky" ends or such that there are "blunt" ends with no overhang. In one aspect, use of restriction enzymes allows cleavage of a plasmid or other expression vector for the purpose of inserting a gene of interest.

A "recognition site" is a double-stranded length of DNA, typically 4 to 8 base pairs long, that a restriction enzyme must recognize in order to cleave DNA. A "restriction site" is the location at which the DNA is cleaved. A restriction site and a recognition site may be the same (i.e., the enzyme cleaves the DNA at the recognition site) or different (i.e., the enzyme cleaves the DNA some distance away from the recognition site). Recognition sites are typically palindromic (either mirror-like palindromes or inverted-repeat palindromes). In one aspect, plasmids typically include restriction sites to aid in the insertion of exogenous genes into the plasmids.

The term "agriculturally acceptable" is used herein to include agricultural, industrial and residential uses which are compatible with plants.

As used herein, the terms "controlling" and "combating" are synonyms. As used herein, by "controlling a pest" or "controls a pest" is intended any effect on a pest that results in limiting the damage that the pest causes. Controlling a pest includes, but is not limited to, killing the pest, inhibiting development of the pest, altering fertility or growth of the pest in such a manner that the pest provides less damage to the plant, or in a manner for decreasing the number of offspring produced, producing less fit pests, producing pests more susceptible to predator attack, or deterring the pests from colonizing the plant. In one aspect, the pest is a microorganism such as, for example, a pathogenic microorganism and/or a microorganism that secretes one or more phytotoxic compounds.

As used herein, the terms "undesirable vegetation", "harmful plants" and "weeds" are synonyms.

As used herein, an "herbicide" is a phytotoxic compound deliberately applied to an area to destroy undesired vegetation (e.g., "weeds"). In one aspect, herbicides are useful for application to agricultural fields so that weeds do not compete with crop plants for resources. In another aspect, a compound is useful as an herbicide if it causes damage to undesired vegetation but not to the agricultural crop or other desired vegetation.

As used herein, the term "herbicide resistant" refers to plants that are resistant to herbicides for example, but not limited to, glyphosate, dicamba, 2,4-dichlorophenoxyethanoic acid, glufosinate, ACCase inhibitors, HPPD inhibitors, acetohydroxyacid synthase inhibitors, thaxtomins, and combinations thereof.

"Adjuvants" are materials that facilitate the activity of herbicides or that facilitate or modify characteristics of herbicide formulations or spray solutions.

As used throughout this application, the term "agriculturally acceptable salt" refers to a salt comprising a cation that is known and accepted in the art for the formation of salts for agricultural or horticultural use. In one aspect, the salt is a water-soluble salt.

The "crops of useful plants" to be protected typically comprise, for example, the following species of plants: cereals (wheat, barley, rye, oats, maize (including field corn, popcorn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fiber plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, for example, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.);

bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. commutate Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)).

The term "useful plants" also includes useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors, thaxtomins, and/or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names Roundu-pReady®, Herculex I® and LibertyLink®.

The term "useful plants" also includes useful plants which have been so transformed by the use of recombinant DNA techniques that they are capable of synthesizing one or more selectively acting toxins, such as are known, for example, from toxin-producing bacteria, especially those of the genus *Bacillus*.

The term "useful plants" also includes useful plants which have been so transformed by the use of recombinant DNA techniques that they are capable of synthesizing antipathogenic substances having a selective action, such as, for example, the so-called "pathogenesis-related proteins" (PRPs, see e.g. EP-A-0 392 225). Examples of such antipathogenic substances and transgenic plants capable of synthesizing such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Unless otherwise specified, temperatures referred to herein are based on atmospheric pressure (i.e. one atmosphere).

Thaxtomins 2,5-Diketopiperazines (DKPs) are a family of small cyclopeptides made of two amino acid monomers. The DKP scaffold is a privileged structure for drug discovery and other applications as it is metabolically stable, structurally constrained, and amenable to multiple stereo-specific modifications. "Thaxtomins" are phytotoxic secondary 2,5-diketopiperazine metabolites produced in plant pathogenic *Streptomyces* strains and have received considerable interests as bioherbicides due to their ability to inhibit cellulose biosynthesis in the nanomolar range (see FIG. 1).

Thaxtomins include a 4-nitroindole moiety that renders them phytotoxic. In one aspect, thaxtomins are produced by pathogenic *Streptomyces* species including, but not limited to, *S. scabies, S. turgidiscabies, S. acidiscabies, S. luridiscabiei, S. puniciscabiei, S. nieviscabei, S. ipomoea*, and other related species. In a further aspect, thaxtomins cause necrosis in plants by inhibiting cellulose synthase. In one aspect, thaxtomins are virulence factors in the disease known as common scab of potato and may also affect sweet potato, beet, carrot, parsnip, radish, rutabaga, turnip, and other commercially-important root crops. In another aspect, thaxtomins can inhibit growth of monocot and dicot seedlings. In still another aspect, thaxtomins are useful as pre- and post-emergent herbicides for broadleaf weeds, sedges, and grassy weeds.

Nitroreductase Enzymes

"Nitroreductases" are members of a family of enzymes that reduce nitrogen-containing compounds, especially compounds having a nitro functional group. Many nitroreductase enzymes require cofactors including, but not limited to, one or more of flavin mononucleotide (FMN), flavin adenine dinucleotide (FAD), nicotinamide adenine dinucleotide (NAD), nicotinamide adenine dinucleotide phosphate (NADP), and the like. In one aspect, a nitroreductase enzyme can reduce a nitro group to an amino group via two putative intermediates. In a further aspect, this reduction can cause a phytotoxic compound such as, for example, a thaxtomin, to lose its phytotoxicity.

In one aspect, disclosed herein is a nitroreductase with specificity for thaxtomin A. In a further aspect, thaxtomin A is the chief thaxtomin species secreted by *S. scabies*, and is primarily responsible for damage caused by potato common scab. In a still further aspect, the nitroreductase can deactivate thaxtomin A by reducing the nitro group of thaxtomin A to an amino group. In one aspect, the nitroreductase gene is isolated from *Haemophilus influenzae* and has SEQ ID NO: 1 or is a derivative or variant thereof such as, for example, a cDNA copy consisting of nitroreductase exons stitched together after introns have been removed. In a further aspect, the nitroreductase gene produces a protein having SEQ ID NO: 4 or a derivative or variant thereof. In another aspect, the nitroreductase protein is known as NfsB. In one aspect, the residues involved in substrate binding may include at least one of R20, W71, S46, C164, G72, G168, E167, K119, Q76, P165, S46, and K106. In another aspect, the residues involved in interacting with FMN include at least one of R16, R209, K207, S18, S45, and R20. In one aspect, DNA and protein sequences useful herein are provided in Table 1:

TABLE 1

Genes and Sequences Useful Herein

| Description | Sequence | SEQ ID NO: |
|---|---|---|
| NfsB gene (*Haemophilus influenzae*) | ATGACTCAACTTACTCGTGAACA AGTTCTTGAACTCTTCCATCAAC GCAGCTCAACACGTTATTACGAC CCAACAAAAAAAATCAGTGATGA AGATTTTGAATGTATTTTAGAGT GCGGTCGATTATCGCCGAGTTCT GTAGGCTCTGAGCCTTGGAAATT TTTAGTGATTCAAAATAAAACCT TACGCGAAAAAATGAAACCTTTT AGCTGGGGAATGATAAATCAGCT TGATAATTGCAGTCATCTTGTGG | 1 |

TABLE 1-continued

Genes and Sequences Useful Herein

| Description | Sequence | SEQ ID NO: |
|---|---|---|
| | TAATTCTCGCGAAGAAAAATGCC CGTTATGATAGTCCGTTTTTGT GGATGTGATGGCACGCAAAGGCT TGAACGCAGAGCAACAACAAGCC GCCCTCACAAAATACAAAGCCCT GCAAGAAGAAGATATGAAATTAC TCGAAAACGACCGCACTTTATTT GATTGGTGCAGCAAACAAACTTA TATCGCCCTTGCAAATATGCTTA CTGGAGCTTCAGCCCTTGGCATC GACTCTTGCCCAATTGAAGGTTT TCATTACGACAAAATGAATGAAT GCCTCGCCGAAGAAGGATTATTC GATCCTCAAGAATATGCGGTTTC TGTCGCCGCAACCTTTGGCTATC GCTCACGCGATATTGCGAAAAAA TCCCGTAAAGGATTGGATGAAGT GGTGAAATGGGTGGGGTAA | |
| NfB-NdeI-F primer | ACTCATATGACTCAACTTACTCG TGAA | 2 |
| NfB-HindIII-R primer | ACTAAGCTTCCCCACCCATTTCA CCACTTCA | 3 |
| NfsB protein | MTQLTREQVLELFHQRSSTRYYD PTKKISDEDFECILECGRLSPSS VGSEPWKFLVIQNKTLREKMKPF SWGMINQLDNCSHLVVILA KKNARYDSPFFVDVMARKG LNAEQQQAALTKYKALQEEDM KLLENDRTLFDWCSKQTYIAL ANMLTGASALGIDSCPIEGFH YDKMNECLAEEGLFDPQEYAV SVAATFGYRSRDIAKKSRKGL DEVVKWVG | 4 |
| NfsB protein putative catalytic domain A | KTLREKMKPFSWGMINQLDN | 5 |
| NfsB protein putative catalytic domain B | KKNARYDSPFFVDVMARKGLNAE QQQAALTKYKALQEEDMKLLEND RTL | 6 |

Figure 6:
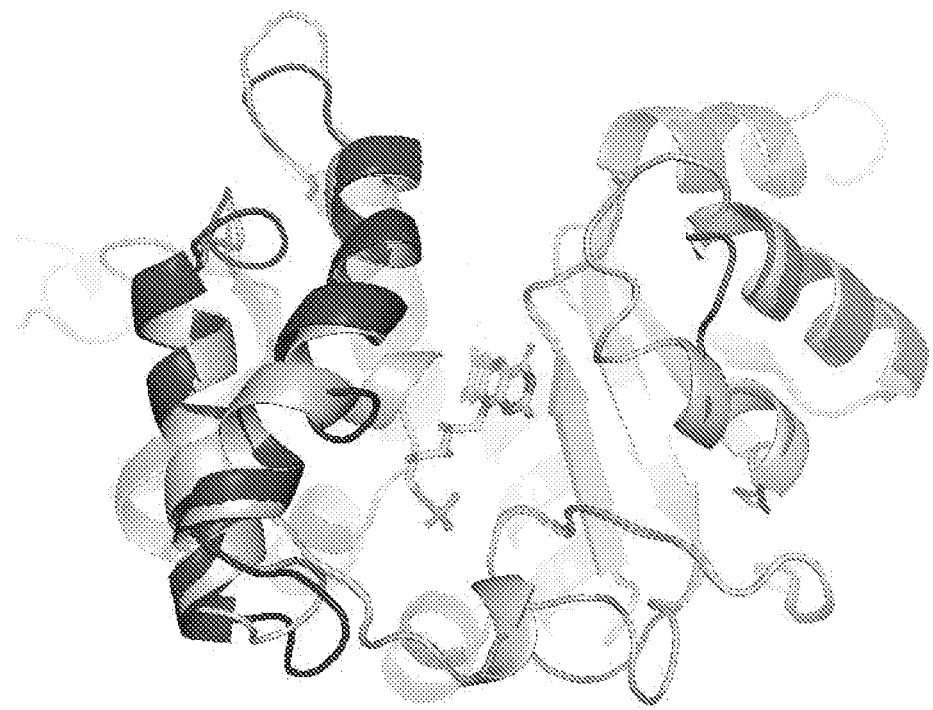
FIG. 6 shows a modeled structure of NfsB from *Haemophilus influenza* prepared using SWISS-MODEL with an NADPH-dependent enzyme from *Vibrio fischeri* as the template (PDB ID: 1VFR). The structures of NfsB (labeled as "C") and the template (labeled as "D") were overlaid; the two loops labeled as "A" and "B" play key roles in catalysis and substrate binding.

In one aspect, the underlined regions in SEQ ID NO: 4 in Table 1 are believed to be especially important for catalysis in the thaxtomin-reducing reactions disclosed herein (see "A" and "B" α-helices in FIG. 6, to which these underlined portions correspond, which correspond, respectively, to the amino acid sequences indicated by the double-underline and dashed underline in the sequence shown above) and to SEQ ID NO: 5 and SEQ ID NO: 6. As used herein, "putative catalytic domain A" and "putative catalytic domain B" refer to SEQ ID NO: 5 and SEQ ID NO: 6, respectively.

In some embodiments, putative catalytic domain A has from about 50% to about 99% sequence identity to the amino acid sequence identified by SEQ ID NO: 5, or has about 50, 55, 60, 65, 70, 75, 80, 85, 90, 91, 92, 93, 94, 95, 96, 97, 98, or about 99% sequence identity to SEQ ID NO: 5, or a combination of any of the foregoing values, or a range encompassing any of the foregoing values. In one aspect, putative catalytic domain A is identical to SEQ ID NO: 5.

In some embodiments, putative catalytic domain B has from about 50% to about 99% sequence identity to the amino acid sequence identified by SEQ ID NO: 6, or has about 50, 55, 60, 65, 70, 75, 80, 85, 90, 91, 92, 93, 94, 95, 96, 97, 98, or about 99% sequence identity to SEQ ID NO: 6, or a combination of any of the foregoing values, or a range encompassing any of the foregoing values. In one aspect, putative catalytic domain B is identical to SEQ ID NO: 6.

In any of these aspects, nitroreductases that have amino acid sequences with substantial homology or sequence identity with SEQ ID NO: 5 and SEQ ID NO: 6 within the overall amino acid sequence for the nitroreductases are especially effective in the methods and processes disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as for producing a nitroreductase enzyme will retain the ability to reduce nitro groups in thaxtomins and related molecules and, in some embodiments, thereby control a pathogenic bacterium of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the present disclosure. Variant polynucleotides also include synthetically derived polynucleotide, such as those generated, for example, by using site-directed mutagenesis, but continue to retain the desired activity. Generally, variants of a particular polynucleotide of the present disclosure (i.e., a nitroreductase gene) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Any region of the polynucleotide of the present disclosure (e.g., the nitroreductase gene) can be used for comparing or determining sequence identity for other polynucleotide sequences useful herein. In one aspect, sequence identity can be determined based on the regions of the polynucleotide sequences corresponding to particular domains of the protein encoded by the polynucleotide, or any combination thereof. In one aspect, sequence identity can be to about 15, 16, 17, 18, 19, 20, 21, 22, 23, 24, 25, 26, 27, 28, 29, or about 30 consecutive nucleotides from nucleotides 1-50, 25-75, 50-100, 75-125, 100-150, 125-175, 150-200, 175-225, 200-250, 225-275, 250-300, 275-325, 300-350, 325-375, 350-400, 375-425, 400-450, 425-475, 450-500, 475-525, 500-550, 525-575, 550-600, 575-625, 600-650, and/or 625-663 of the polynucleotide sequence disclosed herein.

Variants of a particular polynucleotide of the present disclosure (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the present disclosure is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity." As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Protein Variants

As discussed herein, numerous variants of the nitroreductase protein are known and herein contemplated. In addition, to the known functional nitroreductase strain variants there are derivatives of the nitroreductase proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

TABLE 2

Amino Acid Abbreviations

| Amino Acid | Abbreviations | |
| --- | --- | --- |
| Alanine | Ala | A |
| Allosoleucine | AIle | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Phenylalanine | Phe | F |
| Proline | Pro | P |
| Pyroglutamic Acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions

| Original Residue | Exemplary Conservative Substitutions (Others Known in the Art) |
| --- | --- |
| Ala | Ser |
| Arg | Lys; Gln |
| Asn | Gln; His |
| Asp | Glu |
| Cys | Ser |
| Gln | Asn; Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Ley; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions that, in general, are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; (d) a residue having a bulky side chain, e.g., phenylalanine, is substituted for (or by) one not having a side chain, e.g., glycine, in this case; or (e) by increasing the number of sites for sulfation and/or glycosylation.

The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished for example by deleting one of the basic residues or substituting one with glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of a nitroreductase gene and SEQ ID NO: 4 sets forth a particular sequence of a nitroreductase protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Active Fragments of Nitroreductase Sequences

Fragments and variants of the nitroreductase polynucleotides and polypeptides can be employed in the methods and compositions disclosed herein. By "fragment" is intended a portion of the polynucleotide or a portion of the amino acid sequences and, hence, protein encoded thereby. Fragments of a polynucleotide can encode protein fragments that retain nitroreductase activity. Thus, fragments of a nucleotide sequence can range from at least about 20 nucleotides, about 50 nucleotides, about 100 nucleotides, up to the full-length polynucleotide encoding the nitroreductase polypeptides.

A fragment of a nitroreductase polypeptide that encodes a biologically active portion of a nitroreductase polypeptide will encode at least 25, 50, 75, 100, 125, 150, 175, 200, or 220 contiguous amino acids, or up to the total number of amino acids present in a full length nitroreductase polypeptide as set forth in, for example, SEQ ID NO: 4 or an active variant or fragment thereof.

In other embodiments, a fragment of a nitroreductase polynucleotide that encodes a biologically active portion of a nitroreductase polypeptide will encode a region of the polypeptide that is sufficient to form the nitroreductase residue geometry (i.e., putative catalytic domain A and/or putative catalytic domain B) as set forth in SEQ ID Nos. 5 and 6.

In some embodiments, biologically active variants of a nitroreductase polypeptide (and the polynucleotide encoding the same) will have a percent identity across their full length of at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the polynucleotide of SEQ ID NO: 1 or the polypeptide of SEQ ID NO: 4 as determined by sequence alignment programs and parameters described elsewhere herein.

In other embodiments, biologically active variants of a nitroreductase polypeptide (and the polynucleotide encoding the same) will have at least a percent similarity score of at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater to either SEQ ID NO: 1 (for polynucleotides) or SEQ ID NO: 4 (for polypeptides).

The nitroreductase polypeptides and the active variants and fragments thereof may be altered in various ways including amino acid substitutions, deletions, truncations, and insertions and through rational design modeling. Methods for such manipulations are generally known in the art. For example, amino acid sequence variants and fragments of the nitroreductase polypeptides can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference in their entirety. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

In various aspects, the putative catalytic domains (SEQ ID Nos: 5 and 6) can have one or more amino acids changed by site-directed mutagenesis of the correspondencing nucleotide sequence in SEQ ID NO: 4. That is, the amino acid sequence of the putative catalytic domains (SEQ ID Nos: 5 and 6) can be modified to modulate or attenuate nitroreductase activity and/or specificity. For instance, one or more amino acids in one or both catalytic domains can be specifically mutated based on analysis of homologous and/or orthologous catalytic domains, and the mutants screened for activity and specificity. In a further embodiment, the putative catalytic domains (SEQ ID Nos: 5 and 6) can have a level of homology to the unmutated sequence that is about 40%, 75% 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% amino acid homology.

Non-limiting examples of nitroreductases and active fragments and variants thereof are provided herein and can include nitroreductases comprising an active site having catalytic residue geometries shaped by the residues forming putative catalytic domain A and putative catalytic domain B as defined elsewhere herein, or having substantially similar catalytic residue geometries, and further comprising amino acid sequences having at least 40%, 75% 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% percent identity to any one of SEQ ID NOs: 5 and 6, wherein the polypeptide has nitroreductase activity. In an alternative aspect, putative catalytic domain A can have 8, 9, 10, 11, 12, 13, 14, 15, 16, 17, 18, 19, or 20 amino acid matches compared to SEQ ID NO: 5. In another aspect, putative catalytic domain B can have 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 amino acid matches compared to SEQ ID NO: 6.

In other embodiments, the nitroreductases and active fragments and variants thereof are provided herein and can include a nitroreductase that comprises an active site having catalytic residue geometries shaped by the residues forming putative catalytic domain A and putative catalytic domain B as defined elsewhere herein, or having substantially similar catalytic residue geometries, and further comprising amino acid sequences having percent similarity scores of at least 40%, 75% 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater to any one of SEQ ID NOs: 5 or 6, wherein the polypeptide has nitroreductase activity.

Plants Resistant to Thaxtomins

Disclosed herein are compositions and methods for protecting plants from a pathogenic microorganism, such as a *Streptomyces* species or strain, or inducing resistance in a plant to a pathogenic microorganism, such as a *Streptomyces* species or strain.

As used herein, "*Streptomyces* plant pest" is used to refer to any member of the *Streptomyces* genus. Accordingly, the compositions and methods disclosed herein are also useful in protecting plants against any *Streptomyces* plant best including, but not limited to, *Streptomyces* scabies, *Streptomyces turgidiscabies*, *Streptomyces acidiscabies*, *Streptomyces luridiscabiei*, *Streptomyces puniciscabiei*, *Streptomyces nieviscabei*, *Streptomyces ipomoea*, and related organisms.

Those skilled in the art will recognize that not all compositions are equally effective against all pests. Disclosed compositions, including the nitroreductase enzymes disclosed herein, display activity against phytotoxic pathogenic microorganisms, including microorganisms that secrete thaxtomins.

In one aspect, disclosed herein are plants resistant to thaxtomins. In another aspect, the plants incorporate one or more exogenous genes for a nitroreductase enzyme. In another aspect, the exogenous genes have been introduced by any common genetic engineering or genome editing technique known in the art including, but not limited to, use of a biolistic device, a Ti-plasmid, an engineered nuclease (meganucleases, zinc finger nucleases, transcription activator-like effector-based nucleases, and/or CRISPR/Cas9). In still another aspect, the genes are incorporated into the nuclear DNA of the plant, exist on a plasmid (e.g., a Ti-plasmid) inside the plant cell, or are incorporated into mitochondrial or plastid DNA. In any of the above aspects, incorporation of the one or more nitroreductase genes results in production of the nitroreductase enzyme by the plant. In a still further aspect, production of the nitroreductase enzyme by the plant provides the plant with resistance to thaxtomins. In one aspect, production of the nitroreductase enzyme provides the plant with resistance to thaxtomins produced by pests or pathogens. In another aspect, production of the nitroreductase enzyme provides the plant with resistance to thaxtomins incorporated into agricultural compositions such as, for example, herbicides. In still another aspect, production of the nitroreductase enzyme provides the plant with simultaneous resistance to both thaxtomins produced by pests or pathogens and thaxtomins included in agricultural compositions.

In one aspect, crop plants and/or desirable plants expressing nitroreductase enzymes can be planted in a field that has been treated prior to planting with thaxtomins to control weeds or other unwanted plants. In another aspect, a field wherein plants expressing nitroreductase enzymes are growing can be treated with thaxtomins. In one aspect, treating the field with thaxtomins controls and/or kills weeds or other unwanted plants through interference with cellulose synthesis while not damaging the plants expressing nitroreductase, since the nitroreductase expressed by the crop plants or desirable plants inactivates the thaxtomins.

In one aspect, disclosed herein is a plant cell with stably integrated, recombinant DNA including a nucleotide sequence that encodes a nitroreductase protein. In a further aspect, the plant cell also includes a heterologous promoter that is functional in plant cells and that is operably linked to the nucleotide sequence that encodes the nitroreductase protein. In still another aspect, the nucleotide sequence that encodes the nitroreductase protein is isolated from *Haemophilus influenzae, Actinobacillus indolicus, Avibacterium paragallinarum, Mannheimia succiniproducens, Staphylococcus arlettae, Actinobacillus succinogenes*, or *Arcobacter molloscorum*. In another aspect, the nucleotide sequence that encodes the nitroreductase protein is known as NfsB and/or has at least 90% sequence identity with SEQ ID NO: 1, or at least 95% sequence identity with SEQ ID NO: 1, or at least 97% sequence identity with SEQ ID NO: 1. In any of these aspects, the gene can be a cDNA copy of the natural gene (i.e., consisting only of exons and/or coding sequences and with introns, if any, and 5' and/or 3' untranslated regions having been removed).

In another aspect, disclosed herein are transgenic plants, seeds, and/or calluses having a plurality of the plant cells described above as well as their progeny, wherein their progeny plants also include the nucleotide sequence encoding a nitroreductase protein. In one aspect, the transgenic plants and progeny plants are potato plants, beet plants, carrot plants, parsnip plants, radish plants, rutabaga plants, turnip plants, or sweet potato plants. In still another aspect, disclosed herein are vegetables harvested from the transgenic plants.

Exemplary methods for making plants resistant to thaxtomins are provided below.

In another aspect, disclosed herein is a method for reducing a plant damage due to a plant pathogenic organism including providing to a plant or soil before or after introduction of a seed, bulb, tuber, bud, stem, corm, plant part, or a plant, a composition including the DNA construct or expression cassette disclosed herein, wherein the DNA construct or expression cassette includes a nucleotide sequence encoding a nitroreductase protein. In another aspect, disclosed herein is a method for reducing the damage caused by common scab of potato to the roots of a plant including providing to a plant or soil before or after introduction of a seed, bulb, tuber, bud, stem, corm, plant part, or a plant, a composition including the DNA construct, expression cassette, or bacterial or plant host cell disclosed herein, wherein the DNA construct, expression cassette, or host cell includes a nucleotide sequence encoding a nitroreductase protein. In another aspect, disclosed herein is a method for reducing the damage caused by one or more thaxtomins to the roots of a plant including providing to a plant or soil before or after introduction of a seed, bulb, tuber, bud, stem, corm, plant part, or a plant, a composition including the DNA construct, expression cassette, or bacterial or plant host cell disclosed herein, wherein the DNA construct, expression cassette, or host cell includes a nucleotide sequence encoding a nitroreductase protein.

Method of Making a Plant Resistant to Thaxtomin a

DNA Constructs

The use of the term "polynucleotide" is not intended to limit the disclosed polynucleotides to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

The polynucleotide encoding the nitroreductase enzyme or in specific embodiments employed in the methods and compositions of the present disclosure can be provided in expression cassettes for expression in a plant or organism of interest. It is recognized that genes for multiple nitroreductase enzymes including multiple identical nitroreductase enzyme genes or multiple nitroreductase enzyme genes targeting different thaxtomins. In this embodiment, it is recognized that each nitroreductase enzyme gene can be contained in a single or separate cassette, DNA construct, or vector. As discussed, any means of providing the polynucleotide encoding the nitroreductase enzyme is contemplated. A plant or plant cell can be transformed with a single cassette comprising DNA encoding one or more nitroreductase genes or separate cassettes comprising each nitroreductase genes can be used to transform a plant or plant cell or host cell. Likewise, a plant transformed with one component can be subsequently transformed with the second component. One or more nitroreductase genes can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the present disclosure. "Operably linked" is intended to mean a functional linkage between two or more elements. For example, an operable linkage between a polynucleotide of the present disclosure and a regulatory sequence (i.e., a promoter) is a functional link that allows for expression of the polynucleotide of the present disclosure. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the nitroreductase gene employed in the methods and compositions of the present disclosure, and a transcriptional and translational termination region (i.e., termination region) functional in plants. "Divergent promoters" refers to promoters that are oriented in opposite directions of each other, driving transcription of the one or more nitroreductase genes in opposite directions. In another embodiment, one cassette comprising two or more nitroreductase genes under the control of two separate promoters in the same orientation is present in a construct. In another embodiment, two or more individual cassettes, each comprising at least one nitroreductase genes under the control of a promoter, are present in a construct in the same orientation.

The regulatory regions (i.e., promoters, transcriptional regulatory regions, and translational termination regions) and/or the polynucleotides employed in the present disclosure may be native/analogous to the host cell or to each other. Alternatively, the regulatory regions and/or the polynucleotide employed in the present disclosure may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the nitroreductase gene, may be native with the plant host, or may be derived from another source (i.e., foreign or heterologous) to the promoter, the polynucleotide comprising nitroreductase enzyme, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the present disclosure. The polynucleotide encoding the nitroreductase gene can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include those taught in, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, β-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the present disclosure. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6 (2): 141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14 (2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12 (2): 255-265; Kawamata et al. (1997) *Plant Cell Physiol.* 38 (7): 792-803; Hansen et al. (1997) *Mol. Gen Genet.* 254 (3): 337-343; Russell et al. (1997) *Transgenic Res.* 6 (2): 157-168; Rinehart et al. (1996) *Plant Physiol.* 112 (3): 1331-1341; Van Camp et al. (1996) *Plant Physiol.* 112 (2): 525-535; Canevascini et al. (1996) *Plant Physiol.* 112 (2): 513-524; Yamamoto et al. (1994) *Plant Cell Physiol.* 35 (5): 773-778; Lam (1994) *Results Probl. Cell Differ.* 20:181-196; Orozco et al. (1993) *Plant Mol Biol.* 23 (6): 1129-1138; Matsuoka et al. (1993) *Proc Natl. Acad. Sci. USA* 90 (20): 9586-9590; and Guevara-Garcia et al. (1993) *Plant J.* 4 (3): 495-505. Such promoters can be modified, if necessary, for weak expression.

Leaf-preferred promoters are known in the art. See, for example, Yamamoto et al. (1997) *Plant J.* 12 (2): 255-265; Kwon et al. (1994) *Plant Physiol.* 105:357-67; Yamamoto et al. (1994) *Plant Cell Physiol.* 35 (5): 773-778; Gotor et al. (1993) *Plant J.* 3:509-18; Orozco et al. (1993) *Plant Mol. Biol.* 23 (6): 1129-1138; and Matsuoka et al. (1993) *Proc. Natl. Acad. Sci. USA* 90 (20): 9586-9590.

Root-preferred promoters are known and can be selected from the many available from the literature or isolated de novo from various compatible species. See, for example, Hire et al. (1992) *Plant Mol. Biol.* 20 (2): 207-218 (soybean root-specific glutamine synthetase gene); Keller and Baumgartner (1991) *Plant Cell* 3 (10): 1051-1061 (root-specific control element in the GRP 1.8 gene of French bean); Sanger et al. (1990) *Plant Mol. Biol.* 14 (3): 433-443 (root-specific promoter of the mannopine synthase (MAS) gene of *Agrobacterium tumefaciens*); and Miao et al. (1991) *Plant Cell* 3 (1): 11-22 (full-length cDNA clone encoding cytosolic glutamine synthetase (GS), which is expressed in roots and root nodules of soybean). See also Bogusz et al. (1990) *Plant Cell* 2 (7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79 (1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8 (2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29 (4): 759-772); and rolB promoter (Capana et al. (1994) *Plant Mol. Biol.* 25 (4): 681-691. See also U.S. Pat. Nos. 5,837, 876; 5,750,386; 5,633,363; 5,459,252; 5,401,836; 5,110, 732; and 5,023, 179.

In an embodiment, the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this disclosure, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this disclosure include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral (BMC) Biotechnology* 3:7, (www.biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or *Commelina* yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro baciliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application No. 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46 (11): 1779-86), Rice (RSs1) (Shi, T. Wang et al. (1994). *J. Exp. Bot.* 45 (274): 623-631) and maize sucrose synthase-1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196 (3): 564-70., At SAM-1 (S-adenosylmethionine synthetase) (Mijnsbrugge K V. et al. (1996) *Plant Cell. Physiol.* 37 (8): 1108-1115), and the Rice tungro bacilliform virus (RTBV) promoter (Bhattacharyya-Pakrasi et al. (1993) *Plant J.* 4 (1): 71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) Plant Physio/129:913-42), and yellow florescent protein (PhiYFP from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschmidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used with the disclosed polynucleotides, constructs, vectors, methods, and compositions.

In one aspect, disclosed herein is a DNA construct having a nucleotide sequence encoding a nitroreductase protein. In a further aspect, the DNA construct further includes a heterologous promoter that is functional in plant cells and that is operably linked to the nucleotide sequence that encodes the nitroreductase protein. In still another aspect, the nucleotide sequence that encodes the nitroreductase protein is isolated from *Haemophilus influenzae, Actinobacillus indolicus, Avibacterium paragallinarum, Mannheimia succiniproducens, Staphylococcus arlettae, Actinobacillus succinogenes, Arcobacter molloscorum*, or a related organism. In yet another aspect, the nitroreductase protein can be NfsB and/or the sequence that encodes it can have at least 90% sequence identity with SEQ ID NO: 1, at least 95% sequence identity with SEQ ID NO: 1, or at least 97% sequence identity with SEQ ID NO: 1. In some aspects, the nucleotide sequence encoding a nitroreductase protein is a cDNA copy of a natural gene with introns removed.

In another aspect, disclosed herein is an expression cassette containing the DNA construct having a nucleotide sequence encoding a nitroreductase protein. In a further aspect, the nucleotide sequence in the DNA construct is operably linked to a heterologous promoter.

In one aspect, disclosed herein is a plant chromosomal DNA segment that includes a recombinant polynucleotide flanked by native plant DNA, wherein the polynucleotide provides for expression of at least a nitroreductase protein. In another aspect, the plant chromosomal DNA segment includes a recombinant DNA construct for expressing a nitroreductase protein wherein the protein includes contiguous amino acids having at least 90% sequence identity to SEQ ID NO: 4, at least 95% sequence identity to SEQ ID NO: 4, or at least 97% sequence identity to SEQ ID NO: 4. Also disclosed herein are transgenic plant cells including the disclosed plant chromosomal DNA segment. In some aspects, the nitroreductase protein includes portions having SEQ ID NO: 5 and SEQ ID NO: 6, herein referred to as putative catalytic domain A and putative catalytic domain B, respectively, or at least 70% sequence identity thereto, at least 75% sequence identity thereto, at least 80% sequence identity thereto, or at least 85% sequence identity thereto.

In some embodiments, putative catalytic domain A has from about 50% to about 99% sequence identity to the amino acid sequence identified by SEQ ID NO: 5, or has about 50, 55, 60, 65, 70, 75, 80, 85, 90, 91, 92, 93, 94, 95, 96, 97, 98, or about 99% sequence identity to SEQ ID NO: 5, or a combination of any of the foregoing values, or a range encompassing any of the foregoing values. In one aspect, putative catalytic domain A is identical to SEQ ID NO: 5.

In some embodiments, putative catalytic domain B has from about 50% to about 99% sequence identity to the amino acid sequence identified by SEQ ID NO: 6, or has about 50, 55, 60, 65, 70, 75, 80, 85, 90, 91, 92, 93, 94, 95, 96, 97, 98, or about 99% sequence identity to SEQ ID NO: 6, or a combination of any of the foregoing values, or a range encompassing any of the foregoing values. In one aspect, putative catalytic domain B is identical to SEQ ID NO: 6.

In one aspect, disclosed herein is a method for improving resistance to at least one thaxtomin in a crop plant line, the method including providing in the genome of the crop plant the disclosed chromosomal DNA segment. In a further aspect, the thaxtomin is secreted by a pathogenic microorganism such as, for example, *Streptomyces scabies, Streptomyces turgidiscabies, Streptomyces acidiscabies, Streptomyces luridiscabiei, Streptomyces puniciscabiei, Streptomyces nieviscabei, Streptomyces ipomoea*, or a combination thereof.

In an alternative aspect, the thaxtomin can be exogenously applied. In still another aspect, the method improves resistance to both microbially-secreted and exogenously applied thaxtomins simultaneously. In another aspect, the thaxtomin can be thaxtomin A, thaxtomin B, thaxtomin C, and/or thaxtomin D.

Plants, Plant Parts, and Methods of Introducing Sequences into Plants

In one embodiment, the methods of the present disclosure involve introducing a polynucleotide into a plant. "Introducing" is intended to mean presenting to the plant the polynucleotide in such a manner that the sequence gains access to the interior of a cell of the plant. The methods of the present disclosure do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320 334), electroporation (Riggs et al. (1986) *Proc. Natl. Acad. Sci. USA* 83:5602 5606, *Agrobacterium*-mediated transformation (U.S. Pat. Nos. 5,563, 055 and 5,981,840), direct gene transfer (Paszkowski et al. (1984) *EMBO J.* 3:2717 2722), and ballistic particle acceleration (see, for example, U.S. Pat. Nos. 4,945,050; 5,879, 918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923 926); and Lec1 transformation (WO 00/28058). Also see Weissinger et al. (1988) *Ann. Rev. Genet.* 22:421 477; Sanford et al. (1987) *Particulate Science and Technology* 5:27 37 (onion); Christou et al. (1988) *Plant Physiol.* 87:671 674 (soybean); McCabe et al. (1988) *Bio/Technology* 6:923 926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736 740 (rice); Klein et al. (1988) *Proc. Natl. Acad. Sci. USA* 85:4305 4309 (maize); Klein et al. (1988) *Biotechnology* 6:559 563 (maize); U.S. Pat. Nos. 5,240,855; 5,322,783; and, 5,324, 646; Klein et al. (1988) *Plant Physiol.* 91:440 444 (maize); Fromm et al. (1990) *Biotechnology* 8:833 839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the nitroreductase-encoding polynucleotide sequences of the present disclosure can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91:2176-2180 and Hush et al. (1994) *J. Cell Sci.* 107:775-784, all of which are herein incorporated by reference. Alternatively, polynucleotides can be transiently transformed into the plant using techniques known in the art. Such techniques include viral vector systems and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the present disclosure may be introduced into plants by contacting plants with a virus or viral nucleic acids. Generally, such methods involve incorporating a nucleotide construct of the present disclosure within a viral DNA or RNA molecule. Further, it is recognized that promoters of the present disclosure also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931, and Porta et al. (1996) *Mol. Biotechnol.* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the present disclosure can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, provided herein are transformed seed (also referred to as "transgenic seed") having a polynucleotide of the present disclosure, for example, an expression cassette of the present disclosure, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the present disclosure, provided that these parts comprise the introduced polynucleotides.

The compositions, methods, constructs, and polynucleotides may be used for transformation of any plant species including, but not limited to, potato (*Solanum tuberosum*), beet (*Beta vulgaris*), carrot (*Daucus carota*), parsnip (*Pastinaca sativa*), radish (*Raphanus raphanistrum*), rutabaga (*Brassica napobrassica*), turnip (*Brassica rapa* subsp. *Rapa*), and/or sweet potato (*Ipomoea batatas*).

In one aspect, disclosed herein is a host cell containing the DNA construct and/or expression cassette disclosed herein. In some aspects, the host cell can be a bacterial cell. In another aspect, disclosed herein is a plant cell having stably incorporated into its genome a heterologous polynucleotide comprising a nucleotide sequence encoding a nitroreductase protein, wherein the nitroreductase protein is transcribed and translated from a nucleotide sequence having at least 90% sequence identity with SEQ ID NO: 1, at least 95% sequence identity with SEQ ID NO: 1, or at least 97% sequence identity with SEQ ID NO: 1 or a variant or fragment thereof, and wherein the nucleotide sequence encoding the nitroreductase protein, when transcribed and translated, produces a protein capable of reducing a nitro group on a thaxtomin.

Agricultural Products from Transgenic Plants

In one aspect, disclosed herein are agricultural products harvested from transgenic plants produced as described herein. In one aspect, the agricultural products are resistant to diseases such as common scab of potato and related conditions, both before and after harvest. In another aspect, the agricultural products are resistant to cellular damage caused by thaxtomins, both before and after harvest. In still another aspect, the agricultural products are resistant to exogenously-applied agricultural products containing thaxtomins (i.e., herbicides), or are resistant to thaxtomins secreted by pests and/or pathogens, or both. In a further aspect, the agricultural products can be potatoes, sweet potatoes, beets, carrots, parsnips, radishes, rutabagas, turnips, and other common starchy root vegetables susceptible to degradation by thaxtomins.

In any of the above aspects, the agricultural products are safe for human and animal consumption and can be used for any purpose commonly known in the art including food, animal feed, production of natural dyes (e.g., from beets or carrots), production of sugars (e.g., from beets), production of calluses for tissue culture, extraction of starches (e.g., from potato), or the like.

In one aspect, the agricultural products include or are composed of transgenic plant cells capable of expressing one or more nitroreductase enzymes, wherein the nitroreductase enzyme converts one or more thaxtomin nitro groups to an amino group.

Method for Scaling Production of 4-Amino Thaxtomins

In one aspect, disclosed herein is a method for scaling production of 4-amino thaxtomins for use in research and other applications. In one aspect, the method includes the following steps:
  (a) culturing in a culture medium an organism known to produce one or more thaxtomins;
  (b) using the culture medium as a crude extract containing one or more thaxtomins;
  (c) culturing recombinant cells incorporating one or more nitroreductase genes including inducing enzyme production;
  (d) lysing the recombinant cells to release the nitroreductase proteins and form a cell lysate incorporating the same;
  (e) contacting the crude extract containing one or more thaxtomins with a composition containing the lysed recombinant cells to create a mixture;
  (f) incubating the mixture such that the nitroreductase proteins reduce the nitro groups on the thaxtomins to form 4-amino thaxtomins; and
  (g) purifying the 4-amino thaxtomins.

In a further aspect, the reaction can be performed with from about 50 to about 250 ml of reaction mixture, or with about 50, 75, 100, 125, 150, 175, 200, 225, or about 250 ml of reaction mixture, or a combination of any of the foregoing values, or a range encompassing any of the foregoing values. In one aspect, the reaction is performed with about 100 mL of reaction mixture. In another aspect, the reaction mixture includes at least the following components. In one aspect, the reaction mixture includes from about 5 to about 10 mL of cell lysate incorporating nitroreductase proteins, or about 5, 5.5, 6, 6.5, 7, 7.5, 8, 8.5, 9, 9.5, or about 10 mL of cell lysate, or a combination of any of the foregoing values, or a range encompassing any of the foregoing values. In one aspect, 7.5 mL of cell lysate incorporating nitroreductase proteins is used. In another aspect, from about 1 to about 10 mL of crude extract containing thaxtomins is included in the reaction mixture, or about 1, 2, 3, 4, 5, 6, 7, 8, 9, or about 10 mL of crude extract, or a combination of any of the foregoing values, or a range encompassing any of the foregoing values. In one aspect, 2 mL of crude extract containing thaxtomins is used. In a further aspect, the thaxtomins can be suspended in or extracted into DMSO at a concentration of from 15 to 30 mg/mL, or at about 15, 16, 17, 18, 19, 20, 21, 22, 23, 24, 25, 26, 27, 28, 29, or about 30 mg/mL, or a combination of any of the foregoing values, or a range encompassing any of the foregoing values. In another aspect, the crude extract contains about 21.9 mg/ml of thaxtomins in DMSO. In yet another aspect, the crude extract contains from about 60 to about 80% thaxtomin A, or about 60, 61, 62, 63, 64, 65, 66, 67, 68, 69, 70, 71, 72, 73, 74, 75, 76, 77, 78, 79, or about 80% thaxtomin A, or a combination of any of the foregoing values, or a range encompassing any of the foregoing values. In one aspect, the crude extract contains about 69% thaxtomin A, with the remainder including other thaxtomins. In still another aspect, the crude extract includes a buffer such as, for example, 50 mM Tris-HCl buffer in an amount sufficient to maintain the reaction mixture at a pH of 8.0. In another aspect, the reaction mixture includes a flavin mononucleotide (FMN) solution. In one aspect, about 0.5 mL of a 50 mM FMN solution is added to the reaction mixture. In another aspect, the reaction mixture includes an $NADP^+$ solution. In a further aspect, about 2 mL of a 50 mM $NADP^+$ solution is added to the reaction mixture. In still another aspect, the reaction mixture can include other components such as, for example, glutamate dehydrogenase (GDH, 1 mL of an 0.75 mM solution), glucose (1.5 mL of a 40% solution), or other components as described herein or known in the art.

In one aspect, the reaction mixture once formed is incubated at a temperature of from about 30 to about 50° C., or at about 30, 31, 32, 33, 34, 35, 36, 37, 38, 39, 40, 41, 42, 43, 44, 45, 46, 47, 48, 49, or about 50° C., or a combination of any of the foregoing values, or a range encompassing any of the foregoing values. In one aspect, the reaction mixture is incubated at about 37° C. In another aspect, the reaction mixture is incubated for a period of from about 2 to about 10 hours, or for about 2, 3, 4, 5, 6, 7, 8, 9, or about 10 hours, or a combination of any of the foregoing values, or a range encompassing any of the foregoing values. In one aspect, the reaction mixture is incubated for about 6 hours.

In any of the above aspects, the reaction can be terminated by adding a solvent such as, for example, ethyl acetate. In one aspect, the volume of ethyl acetate added to the reaction mixture is equal to the total volume of the reaction mixture. In a further aspect, the mixture can be extracted one, two, three, or four times with ethyl acetate. In any of these aspects, the organic layer can from each extraction can be combined, washed with water, dried, and evaporated. In still another aspect, the residue left after evaporation can be purified by a method known in the art such as, for example, high pressure liquid chromatography (HPLC). In still another aspect, HPLC fractions containing the product of interest can be combined and lyophilized to yield solid 4-amino thaxtomins.

Agricultural Compositions Containing Thaxtomins Formulations

The present disclosure also concerns agricultural compositions comprising or consisting essentially of an active compound such as, for example, a thaxtomin, as described herein in combination with a suitable carrier (e.g., an agricultural carrier) or adjuvant (e.g., and agricultural adjuvant). In some aspects, the disclosed agricultural compositions are useful as herbicidal compositions for use with commercially useful plants and crops, including crops of useful plants.

The agricultural composition of the present disclosure, e.g., a disclosed herbicidal composition, can contain from 0.1 to 99% by weight, e.g., from 0.1 to 95% by weight, of a disclosed compound, 99.9 to 1% by weight, e.g., 99.8 to 5% by weight, of a solid or liquid adjuvant, and optionally from 0 to 25% by weight, e.g., from 0.1 to 25% by weight, of a surfactant.

The agricultural composition of the present disclosure, e.g., a disclosed herbicidal composition, can contain from 0.1 to 99% by weight, e.g., from 0.1 to 95% by weight, of a disclosed compound, 99.9 to 1% by weight, e.g., 99.8 to 5% by weight, of a solid or liquid carrier, and optionally from 0 to 25% by weight, e.g., from 0.1 to 25% by weight, of a surfactant.

Suitably, an agricultural composition of the present disclosure, e.g., a disclosed herbicidal composition, can be applied at any suitable developmental stage of the crop or plant. Rates and frequency of use of the formulations are those conventionally used in the art and factors such as the developmental stage of the plant and on the location, timing and application method, and density and development stage of the undesirable plant, e.g., a weed. Advantageous rates of application can range from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds.

In practice, as indicated above, an agricultural composition of the present disclosure, e.g., a disclosed herbicidal composition, can be applied as a formulation containing the various adjuvants and carriers known to or used in the industry. They may thus be formulated as granules, as wettable or soluble powders, as emulsifiable concentrates, as coatable pastes, as dusts, as flowables, as solutions, as suspensions or emulsions, or as controlled release forms such as microcapsules. These formulations are described in more detail below and may contain as little as about 0.5% to as much as about 95% or more by weight of the active ingredient. The optimum amount will depend on formulation, application equipment and nature of the plant to be treated. In addition, the disclosed agricultural compositions, e.g., an herbicidal composition, can optionally further comprise conventional additives such as surfactants, drift reduction agents, safeners, solubility enhancing agents, thickening agents, flow enhancers, foam-moderating agents, freeze protectants, UV protectants, preservatives, antimicrobials, and/or other additives that are necessary or desirable to improve the performance, crop safety, or handling of the composition.

Suitable agricultural adjuvants and carriers that are useful in formulating the compositions of the present disclosure in the formulation types described above are well known to those skilled in the art. Other adjuvants commonly utilized in agricultural compositions include crystallization inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralizing agents and buffers, corrosion inhibitors, dyes, odorants, spreading agents, penetration aids, micronutrients, emollients, lubricants, sticking agents, and the like. Suitable examples of the different classes are found in the non-limiting list below.

Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+ emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, C9-C11 alkylpolyglycoside or less, phosphate alcohol ethoxylate or less, natural primary alcohol (C12-C16) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG (400) dioleate-99.

In some aspects, the additive is a safener that is an organic compound leading to better crop plant compatibility when applied with an herbicide. In some aspects, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenyl-sulfonylbenzoic acid amides, as well as agriculturally acceptable salts and, provided they have a carboxyl group, their agriculturally acceptable derivatives thereof. In some aspects, the safener can be cloquintocet or an ester or salt thereof, such as cloquintocet (mexyl). For example, cloquintocet can be used to antagonize harmful effects of the compositions on rice and cereals.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N, N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaceous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application, including surfactants. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C 18 ethoxylate; alcohol-alkylene oxide addition products, such as tridecyl alcohol-C 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Suspension concentrates are aqueous formulations in which finely divided solid particles of the active compound are suspended. Such formulations include anti-settling agents and dispersing agents and may further include a wetting agent to enhance activity as well an antifoam and a crystal growth inhibitor. In use, these concentrates are diluted in water and normally applied as a spray to the area to be treated. The amount of active ingredient, i.e., one or more disclosed compound, may range from about 0.5% to about 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent. Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 mm to 1 cm and preferably 1 to 2 mm in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes, and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, may also be used.

In addition, further, other biocidally active ingredients or compositions may be combined with the disclosed compound and used in the methods of the present disclosure and applied simultaneously or sequentially with the disclosed compound. When applied simultaneously, these further active ingredients may be formulated together with the disclosed compound or mixed in, for example, the spray tank. These further biocidally active ingredients may be fungicides, herbicides, insecticides, bactericides, acaricides, nematicides and/or plant growth regulators.

Accordingly, the present disclosure provides for the use of a composition in the methods of the present disclosure, said composition comprising (i) a disclosed compound and (i) a fungicide, (ii) an herbicide, (iii) an insecticide, (iv) a bactericide, (v) an acaricide, (vi) a nematicide and/or (vii) a plant growth regulator.

The herbicidal compositions of the present disclosure optionally can further comprise at least one non-auxin herbicide. The term "non-auxin herbicide" refers to an herbicide having a primary mode of action other than as an auxin herbicide. Representative examples of non-auxin herbicides include acetyl COA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, and nucleic acid inhibitors; salts and esters thereof; racemic mixtures and resolved isomers thereof; and combinations thereof.

Representative examples of ACCase inhibitors include clethodim, clodinafop, fenoxaprop-P, fluazifop-P, quizalofop-P, and sethoxydim.

Representative examples of ALS or AHAS inhibitors include flumetsulam, imazamethabenz-m, imazamox, imazapic, imazapyr, imazaquin, imazethapyr, metsulfuron, prosulfuron, and sulfosulfuron.

Representative examples of photosystem I inhibitors include diquat and paraquat.

Representative examples of photosystem II inhibitors include atrazine, cyanazine, diuron, and metibuzin.

Representative examples of PPO inhibitors include acifluorofen, butafenacil, carfentrazone-ethyl, flufenpyr-ethyl, fluthiacet, flumiclorac, flumioxazin, fomesafen, lactofen, oxadiazon, oxyfluorofen, and sulfentrazone.

Representative examples of carotenoid biosynthesis inhibitors include aclonifen, amitrole, diflufenican, mesotrione, and sulcotrione.

A representative example of an EPSP inhibitor is N-phosphonomethyl glycine (glyphosate).

A representative example of a glutamine synthetase inhibitor is glufosinate.

A representative example of a dihydropteroate synthetase inhibitor is asulam.

Representative examples of mitosis inhibitors include acetochlor, alachlor, dithiopyr, S-metolachlor, and thiazopyr.

Representative examples of nucleic acid inhibitors include difenzoquat, fosamine, metham, and pelargonic acid.

In one aspect, the herbicidal compositions of the present disclosure further comprise a non-auxin herbicide selected from the group consisting of acetochlor, glyphosate, glufosinate, flumioxazin, fomesafen, and agriculturally acceptable salts thereof.

In one aspect, the herbicidal compositions of the present disclosure further comprise glyphosate, or an agriculturally acceptable salt thereof. Suitable glyphosate salts include, for example, the ammonium, diammonium, dimethylammonium, monoethanolamine, isopropylamine, and potassium salts, and combinations thereof. In one aspect, the glyphosate salts are selected from the group consisting of monoethanolamine, isopropylamine, and potassium salts, and combinations thereof.

In one aspect, the herbicidal compositions of the present disclosure further comprise glufosinate, or an agriculturally acceptable salt thereof.

In one aspect, the herbicidal compositions of the present disclosure can further comprise dicamba, or an agriculturally acceptable salt or ester thereof, and glyphosate, or an agriculturally acceptable salt thereof. In another aspect, the herbicidal compositions of the present disclosure comprise dicamba, or an agriculturally acceptable salt thereof; glyphosate, or an agriculturally acceptable salt thereof; and a non-ammoniated, agriculturally acceptable acetate salt. Commercially available sources of glyphosate, and its agriculturally acceptable salts, include those products sold under the trade names DURANGO® DMAR, HONCHO PLUS®, ROUNDUP POWERMAX®, ROUNDUP WEATHERMAX®, TRAXION®, and TOUCHDOWN®.

In one aspect, the herbicidal compositions of the present disclosure can further comprise 2,4-D, or an agriculturally acceptable salt or ester thereof, and glyphosate, or an agriculturally acceptable salt thereof. In another aspect, the herbicidal compositions of the present disclosure comprise 2,4-D, or an agriculturally acceptable salt or ester thereof; glyphosate, or an agriculturally acceptable salt thereof; and a non-ammoniated, agriculturally acceptable acetate salt.

In some aspects, the disclosed herbicidal compositions can further comprise an additive such as a pesticide. Exemplary pesticides include, but are not limited to, 2,4-D, acetochlor, aclonifen, amicarbazone, 4-aminopicolinic acid based herbicides, such as halauxifen, halauxifen-methyl, and those described in U.S. Pat. Nos. 7,314,849 and 7,432,227 to Balko, et al., amidosulfuron, aminocyclopyrachlor, aminopyralid, aminotriazole, ammonium thiocyanate, anilofos, asulam, azimsulfuron, atrazine, beflubutamid, benazolin, benfuresate, bensulfuron-methyl, bentazon-sodium, benzofenap, bifenox, bispyribac-sodium, bromobutide, bromacil, bromoxynil, butachlor, butafenacil, butralin, butroxydim, carbetamide, cafenstrole, carfentrazone, carfentrazone-ethyl, chlormequat, clopyralid, chlorsulfuron, chlortoluron, cinidon-ethyl, clethodim, clodinafop-propargyl, clomeprop, clomazone, cloransulam-methyl, cyanazine, cyclosulfamuron, cycloxydim, cyhalofop-butyl, daimuron, dicamba, dichlobenil, dichlorprop-P, diclofop-methyl, diclosulam, diflufenican, diflufenzopyr, dimefuron, dimethachlor, diquat, diuron, S-ethyl dipropylcarbamothioate (EPTC), esprocarb, ethoxysulfuron, etobenzanid, fenoxaprop, fenoxaprop-ethyl, fenoxaprop-ethyl+isoxadifen-ethyl, fenoxaprop-P-ethyl, fenoxasulfone, fenquinotrione, fentrazamide, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, flurochloridone, fluroxypyr, fluroxypyr-meptyl, flurtamone, glufosinate, glufosinate-ammonium, glyphosate, halosulfuron-methyl, haloxyfop-methyl, haloxyfop-R-methyl, hexazinone, imazamethabenz, imazamox, imazapic, imazapyr, imazaquin, imazethapyr, imazosulfuron, indanofan, indaziflam, iodosulfuron, iodosulfuron-ethyl-sodium, iofensulfuron, ioxynil, ipfencarbazone, isoproturon, isoxaben, isoxaflutole, lactofen, linuron, MCPA, MCPB, mecoprop-P, mefenacet, mesosulfuron, mesosulfuron-ethyl sodium, mesotrione, metamifop, metazochlor, metazosulfuron, metosulam, metribuzin, metsulfuron, metsulfuron-methyl, molinate, MSMA, napropamide, napropamide-M, orfurazon, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, pinoxaden, pretilachlor, primisulfuron, profluazol, profoxydim, propanil, propaquizafop, propyrisulfuron, propoxycarbazone, propyzamide, prosulfocarb, prosulfuron, pyraclonil, pyraflufen-ethyl, pyrasulfotole, pyrazosulfuron-ethyl, pyrazolynate, pyribenzoxim (LGC-40863), pyributicarb, pyridate, pyriftalid, pyrimisulfan, pyroxsulam, pyroxasulfone, quinclorac, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tefuryltrione, tepraloxidim, terbacil, terbuthylazine, terbutryn, thenylchlor, thiazopyr, thifensulfuron, thifensulfuron-methyl, thiobencarb, topramezone, tralkoxydim, triafamone, triasulfuron, tribenuron, tribenuron-methyl, triafamone, triclopyr, and trifluralin, and agriculturally acceptable salts, choline salts, esters and mixtures thereof. In certain aspects, the additional pesticide includes benzofenap, cyhalofop, daimuron, pentoxazone, esprocarb, pyrazosulfuron, butachlor, pretilachlor, metazosulfuron, bensulfuron-methyl, imazosulfuron, azimsulfuron, bromobutide, benfuresate, mesotrione, oxazichlomefone, and agriculturally acceptable salts or esters thereof, or combinations thereof. In certain aspects, the additional pesticide includes triclopyr choline salt.

Methods of Using

The agricultural compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some aspects, the method of application can be chosen to ensure the finest possible distribution of the compositions disclosed herein.

The agricultural compositions disclosed herein can be applied pre-emergence (before the emergence of undesirable vegetation) or post-emergence (i.e., during and/or after emergence of the undesirable vegetation). The composition can be applied, for example, to the vegetation as an in-water application to an irrigated potato field.

When the agricultural compositions are used in crops, the compositions can be applied after seeding and before or after the emergence of the crop plants. In some aspects, the compositions disclosed herein show good crop tolerance even when the crop has already emerged, and can be applied during or after the emergence of the crop plants. In some aspects, when the compositions are used in crops, the compositions can be applied before seeding of the crop plants.

In some aspects, the compositions disclosed herein are applied to vegetation or an area adjacent the vegetation, or applied to soil, or applied to/into water, for example to/into an irrigation water source for a crop, to prevent the emergence or growth of vegetation by spraying (e.g., foliar spraying). In some aspects, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some aspects, the compositions disclosed herein are applied by the low-volume or the ultra-low-volume method, wherein the application is in the form of micro granules. In some aspects, the compositions disclosed herein can be applied as dry formulations (e.g., granules, WDGs) into water.

The compositions and methods disclosed herein can be used to control undesired vegetation in a variety of crop and non-crop applications. In some aspects, the compositions and methods disclosed herein can be used for controlling undesired vegetation in potatoes (e.g., in potatoes grown from seed potatoes, potato plants grown from callus or tissue culture, or the like).

Method for Scaling Production of Nitroreductase Enzymes

In one aspect, disclosed herein are methods for scaling production of nitroreductase enzymes for commercial use and/or for use in further studies. In a further aspect, the nitroreductases of interest can be from any organism that produces a nitroreductase enzyme. In a further aspect, the nitroreductase can be from *Haemophilus influenzae, Actinobacillus indolicus, Avibacterium paragallinarum, Mannheimia succiniproducens, Staphylococcus arlettae, Actinobacillus succinogenes, Arcobacter molloscorum*, or a related organism. In one aspect, the nitroreductase is from *H. influenzae*. In some aspects, the nitroreductase gene has SEQ ID NO: 1. In any of the above aspects, primers for amplifying the chosen nitroreductase gene and/or cDNA can be chosen by the skilled artisan. In one aspect, the primers can be SEQ ID NO: 2 (NfB-NdeI-F) and SEQ ID NO: 3 (NfB-HindIII-R) or other primers matching the ends of the area of DNA to be copied using the polymerase chain reaction (PCR). PCR can be carried out using established protocols. Following PCR, in some aspects, the PCR product can be purified by known techniques and digested with restriction enzymes such as, for example, NdeI and HindIII, where the restriction enzymes have recognition sites in the primers.

In a further aspect, a plasmid can be selected for incorporation of the cloned gene. In one aspect, the plasmid is pWLneo, pSV2cat, pOG44, pXT1, PSG, pSVK3, pBSK, pBSKII, pUC, pUC19, pETDuet-1, or pET22b. In one aspect, the plasmid is pET22b. In another aspect, the plasmid is digested with the same restriction enzymes (e.g., NdeI and HindIII or another pair). Following digestion, the amplified DNA and/or the plasmid can be separated from unwanted side product, for example, by agarose gel electrophoresis followed by purification and extraction techniques. In another aspect, digested cloned DNA (i.e., the nitroreductase gene) and the digested plasmid can be ligated to form an expression vector containing the DNA of interest. In one aspect, successful insertion of the cloned gene can be established by sequencing the expression vector.

In another aspect, established transformation protocols can be used in order to insert the expression vector into a host bacterial cell such as, for example, E. coli. In one aspect, successful transformation can be assessed by culturing the host bacterial cells in a medium incorporating an antibiotic such as, for example, ampicillin, where the expression vector contains a gene for resistance to ampicillin or another antibiotic and where only cells that have been transformed are resistant to the antibiotic. In a further aspect, following transformation, the host bacterial cells can be cultured in any acceptable medium. In a further aspect, host bacterial cells are cultured in a medium containing an antibiotic so that non-transformed cells do not compete with transformed cells for resources. In any of these aspects, when a desired cell concentration is reached, protein expression can be induced. In one aspect, the desired cell concentration is from about 0.4 to 0.8 at 600 nm (i.e., $OD_{600}$ is from about 0.4 to about 0.8), or is about 0.4, 0.45, 0.5, 0.55, 0.6, 0.65, 0.7, 0.75, or about 0.8, or a combination of any of the foregoing values, or a range encompassing any of the foregoing values. In one aspect, $OD_{600}$ is about 0.6. In another aspect, protein expression can be induced with isopropyl β-D-1-thiogalactopyranoside (IPTG). In one aspect, induction can occur at a temperature of from about 15 to about 20° C., or at about 15, 16, 17, 18, 19, or about 20° C., or a combination of any of the foregoing values, or a range encompassing any of the foregoing values. In one aspect, induction occurs at about 18° C. In another aspect, induction takes place with shaking at from about 150 to about 250 rpm, or about 150, 160, 170, 180, 190, 200, 210, 220, 230, 240, or about 250 rpm, or a combination of any of the foregoing values, or a range encompassing any of the foregoing values. In one aspect, induction takes place with shaking at 190 rpm. In still another aspect, induction occurs for from about 16 to about 24 hours, or for about 16, 17, 18, 19, 20, 21, 22, 23, or about 24 hours, or a combination of any of the foregoing values, or a range encompassing any of the foregoing values. In one aspect, induction occurs for about 20 hours.

In any of the above aspects, following induction of protein production, cells are centrifuged and pellets produced. In one aspect, centrifugation is conducted at from about 4000 to about 6000 rpm, or about 4000, 4100, 4200, 4300, 4400, 4500, 4600, 4700, 4800, 4900, 5000, 5100, 5200, 5300, 5400, 5500, 5600, 5700, 5800, 5900, or about 6000 rpm, or a combination of any of the foregoing values, or a range encompassing any of the foregoing values. In one aspect, centrifugation is conducted at about 5000 rpm. In another aspect, centrifugation is conducted for from about 5 to about 15 minutes, or for about 5, 6, 7, 8, 9, 10, 11, 12, 13, 14, or about 15 minutes, or a combination of any of the foregoing values, or a range encompassing any of the foregoing values. In one aspect, centrifugation is conducted for about 10 min. In still another aspect, centrifugation is conducted at a temperature of from about 2 to about 8° C., or at about 2, 3, 4, 5, 6, 7, or about 8° C., or a combination of any of the foregoing values, or a range encompassing any of the foregoing values. In one aspect, centrifugation is conducted at about 4° C. In any of the above aspects, following centrifugation, cell pellets can be resuspended in an appropriate lysis buffer. In one aspect, the lysis buffer can include 25 mM Tris·HCl, 100 mM NaCl, 10 mM imidazole, 3 mM β-mercaptoethanol, and 10% glycerol, with a pH of about 7.5. Slight variations and modifications of these values are also effective. In another aspect, the cell biomass: buffer volume ratio can be from about 1:1 to about 1:10, or can be about 1:1, 1:2, 1:3, 1:4, 1:5, 1:6, 1:7, 1:8, 1:9, or about 1:10, or a combination of any of the foregoing values or a range encompassing any of the foregoing values. In one aspect, the cell biomass: buffer volume ratio is about 1:4. In a still further aspect, following contact with the lysis buffer, soluble proteins can be released from the cell pellets by sonication. In still another aspect, following sonication, centrifugation can again be performed to collect the soluble proteins. In one aspect, centrifugation occurs at from about 15,000 to about 20,000 rpm, or at about 15,000, 15,500, 16,000, 16,500, 17,000, 17,500, 18,000, 18,500, 19,000, 19,500, or about 20,000 rpm, or a combination of any of the foregoing values or a range encompassing any of the foregoing values. In one aspect, centrifugation occurs at about 18,000 rpm. In another aspect, centrifugation is conducted at a temperature of from about 2 to about 8° C., or at about 2, 3, 4, 5, 6, 7, or about 8° C., or a combination of any of the foregoing values, or a range encompassing any of the foregoing values. In one aspect, centrifugation is conducted at about 4° C. In still another aspect, centrifugation can be carried out for from about 30 minutes to about 1 hour, or for about 30, 35, 40, 45, 50, 55, or about 60 minutes, or a combination of any of the foregoing values, or a range encompassing any of the foregoing values. In one aspect, centrifugation is conducted for about 40 min.

In another aspect, further purification can be accomplished using an appropriate resin. In one aspect, a Ni-NTA agarose resin can be used for protein purification using procedures established in the art. In some aspects, the resin suppliers also provide instructions for using the resins. In one aspect, purified recombinant proteins can be exchanged into a storage buffer following purification. In one aspect, the storage buffer can include at least the following components: 25 mM Tris·HCl, 50 mM NaCl, 10% glycerol. Variations of these concentrations are also envisioned. In another aspect, the storage buffer has pH 8.0. In still another aspect, a desalting column such as, for example, a PD-10 column, can be used to exchange the recombinant proteins into the storage buffer. In any of the above aspects, following purification and buffer exchange, the recombinant nitroreductase enzymes can be aliquoted and stored at −80° C. until use. In one aspect, protein concentrations can be determined by any method known in the art including, but not limited to, UV-Vis spectrophotometry. In some aspects, SDS-PAGE analysis or another method can be used to show the recombinant protein has the expected size.

Compositions Containing Nitroreductase Genes and/or Proteins

One or more of the polynucleotides encoding a nitroreductase gene and/or one or more nitroreductase proteins can be provided as an external composition such as a spray or powder to the plant, plant part, seed, a pest, or an area of cultivation. In another example, a plant is transformed with a DNA construct or expression cassette for expression of at least one nitroreductase gene. In either composition, the nitroreductase gene, when contacted by a thaxtomin, can reduce the nitro group on the thaxtomin and render it non-phytotoxic. It is recognized that the composition can comprise a cell (such as plant cell or a bacterial cell), in which a polynucleotide encoding the nitroreductase gene is stably incorporated into the genome and operably linked to promoters active in the cell. Compositions comprising a mixture of cells, some cells expressing at least one nitroreductase gene are also encompassed. In other embodiments, compositions comprising the nitroreductase genes and/or proteins are not contained in a cell. In such embodiments, the composition can be applied to an area inhabited by a pathogenic bacterium such as one that secretes thaxtomins. In one embodiment, the composition is applied externally to a plant (i.e., by spraying a field or area of cultivation) to protect the plant from the pathogenic bacterium. Methods of applying polynucleotides and/or proteins in such a manner are known to those of skill in the art.

The composition comprising the nitroreductase gene and/or protein can be formulated in an agriculturally suitable and/or environmentally acceptable carrier. Such carriers can be any material that the animal, plant or environment to be treated can tolerate. Furthermore, the carrier must be such that the composition remains effective at controlling a pathogenic microorganism and/or reducing plant damage from thaxtomins secreted by the microorganism. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Various insecticidal formulations can also be found in, for example, US Publications 2008/0275115, 2008/0242174, 2008/0027143, 2005/0042245, and 2004/0127520, each of which is herein incorporated by reference.

It is recognized that the polynucleotides comprising sequences encoding the nitroreductase gene can be used to transform organisms to provide for host organism production of this components, and subsequent application of the host organism to the environment of the target pathogenic microorganisms. Such host organisms include baculoviruses, bacteria, and the like. In this manner, the combination of polynucleotides encoding the nitroreductase gene may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the nitroreductase protein, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes*, fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing the polynucleotide comprising the nitroreductase gene into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3rd ed.; Cold Spring Harbor Laboratory Press, Plainview, NY); Davis et al. (1980) *Advanced Bacterial Genetics* (Cold Spring Harbor Laboratory, Cold Spring Harbor, NY); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella,* and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum; Lactobacillus*; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces,* and the like.

Characteristics of particular interest in selecting a host cell for purposes of the present disclosure include ease of introducing the coding sequence into the host, availability of expression systems, efficiency of expression, stability in the host, and the presence of auxiliary genetic capabilities. Characteristics of interest for use as a pathogen-control microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the nitroreductases encompassed by the present disclosure can be introduced into microorganisms that multiply on plants (epiphytes) to deliver these components to potential target pests. Epiphytes, for example, can be gram-positive or gram-negative bacteria.

The nitroreductase gene can be fermented in a bacterial host and the resulting bacteria processed and used as a microbial spray in the same manner that *Bacillus thuringiensis* strains have been used as insecticidal sprays. Any suitable microorganism can be used for this purpose. By way of example, *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the present disclosure are produced by introducing heterologous genes into a cellular host. Expression of the heterologous sequences results, directly or indirectly, in the intracellular production of the nitroreductase protein(s). These compositions may then be formulated in accordance with conventional techniques for application to the environment hosting a target pest, e.g., soil, water, and foliage of plants. See, for example, EPA 0192319, and the references cited therein.

As disclosed herein, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients disclosed herein (i.e., at least one nitroreductase enzyme) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one nitroreductase enzymeinclude, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the nitroreductase proteins can be in a suitable form for direct application or as a concentrate of primary composition that requires dilution with a suitable quantity of water or other dilutant before application.

The compositions (including the transformed microorganisms) can be applied to the environment of a plant pathogenic microorganism (e.g., a *Streptomyces* species that produces a thaxtomin) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pathogenic microorganisms in the early stages of plant growth, as this is the time when the plant can be most severely damaged. In some aspects, thaxtomins can be particularly damaging to emergent plant seedlings. The compositions can conveniently contain another insecticide if this is thought necessary. In an embodiment of the present disclosure, the composition(s) is applied directly to the soil, at a time of planting, in granular form of a composition of a carrier and dead cells of a *Bacillus* strain or transformed microorganism of the present disclosure. Another embodiment is a granular form of a composition comprising an agrochemical such as, for example, an herbicide, an insecticide, a fertilizer, in an inert carrier, and dead cells of a *Bacillus* strain or transformed microorganism of the present disclosure.

Figure 2:
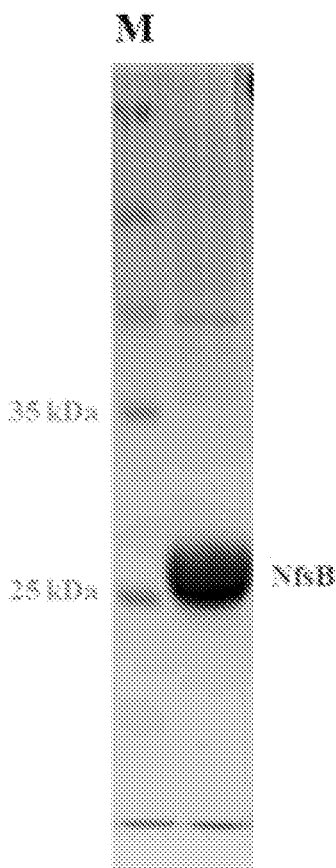
FIG. 2 shows SDS-PAGE analysis of purified recombinant NfsB. M: marker.
Figure 3A:
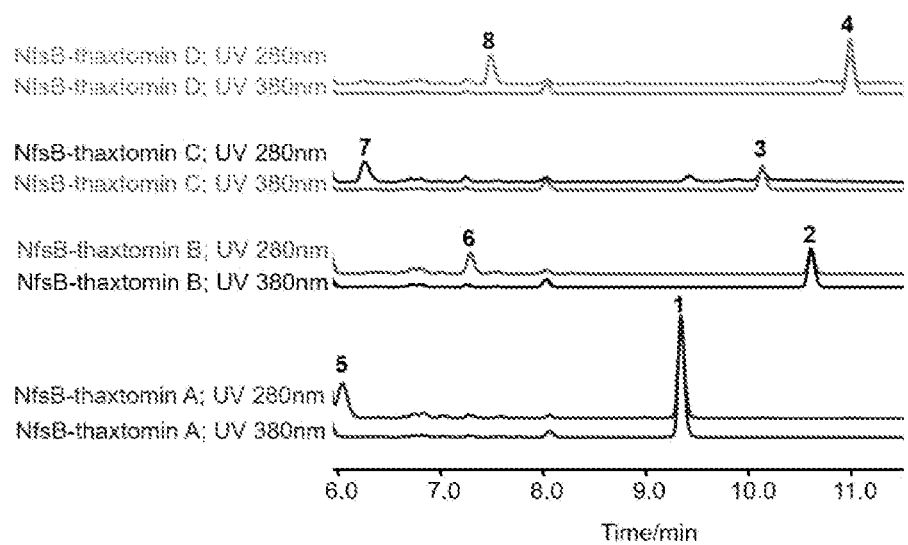
FIGS. 3A-3B show HPLC and LC-MS spectra of 4-amino-thaxtomins produced in the NfsB reactions.
Figure 3B:
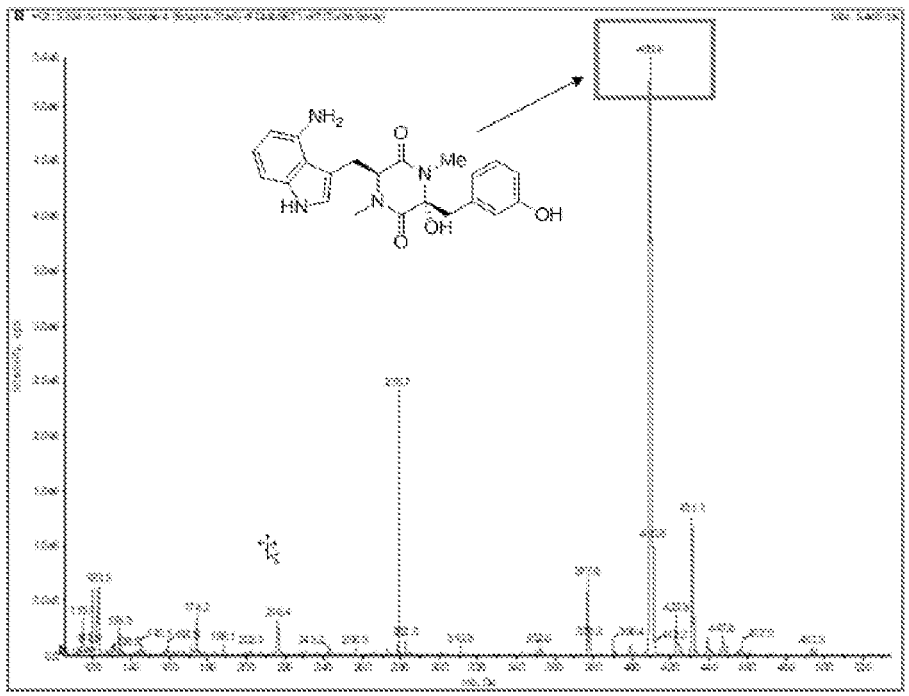
Figure 3C:
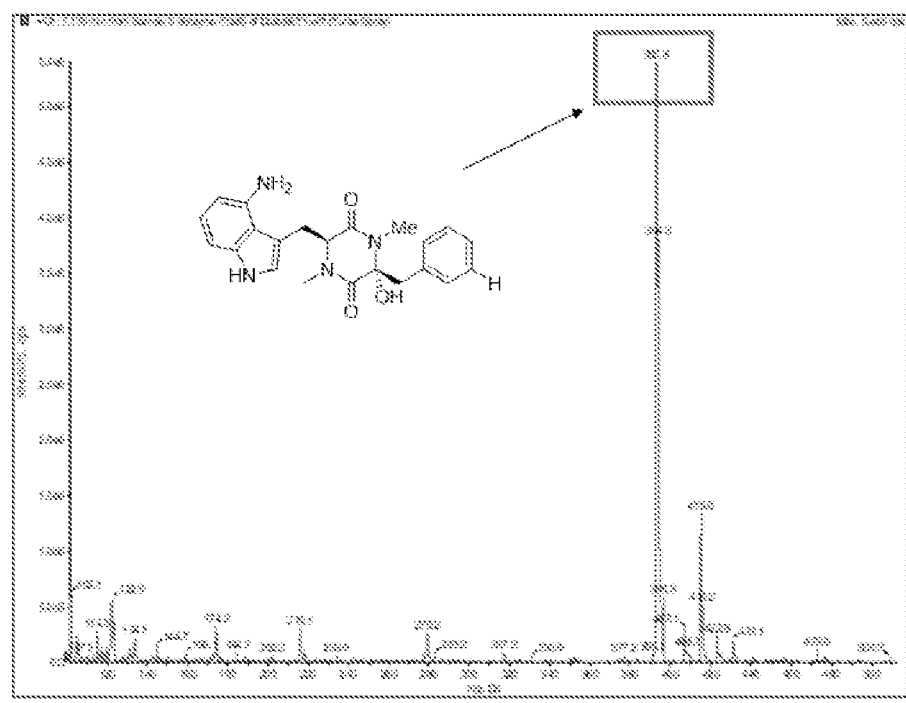
FIG. 3C. LC-MS detection of the $[M+1]^+$ peak of compound 6, which is indicated in the box.
Figure 3D:
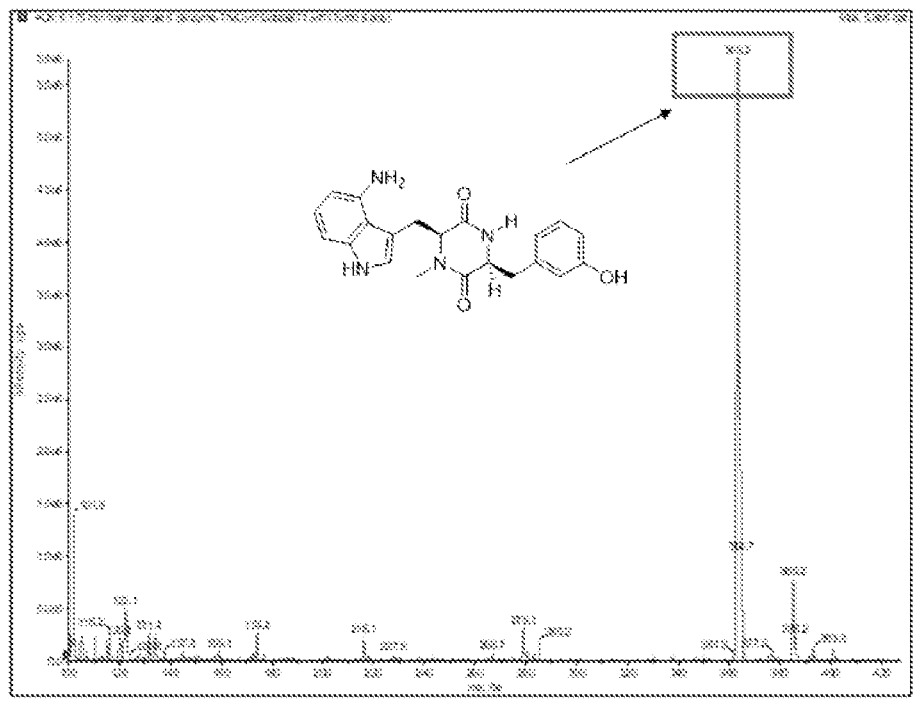
FIG. 3D. LC-MS detection of the $[M+1]^+$ peak of compound 7, which is indicated in the box.
Figure 3E:
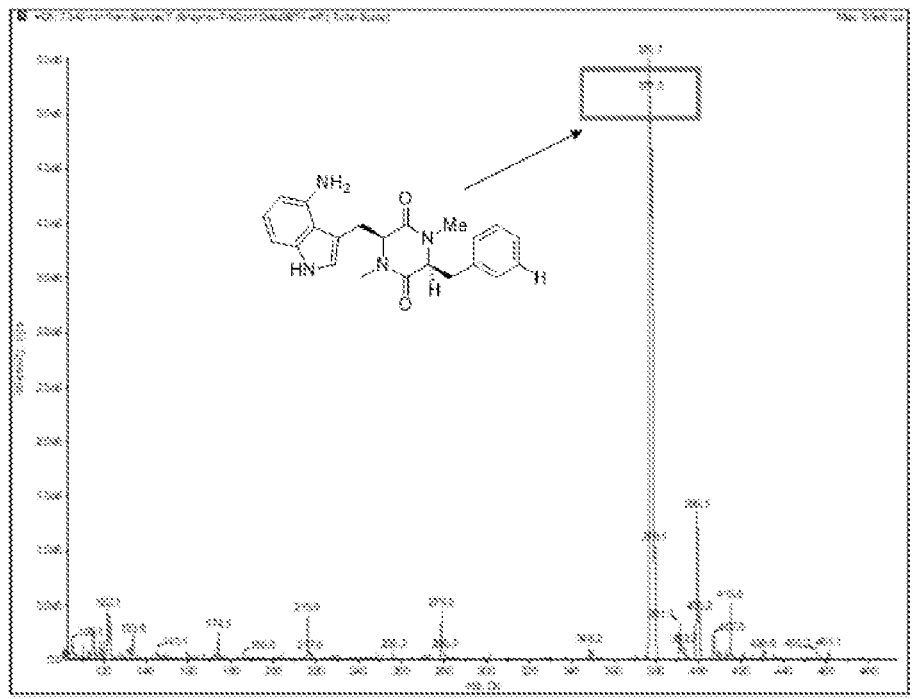
FIG. 3E. LC-MS detection of the $[M+1]^+$ peak of compound 8, which is indicated in the box.
Figure 4A:
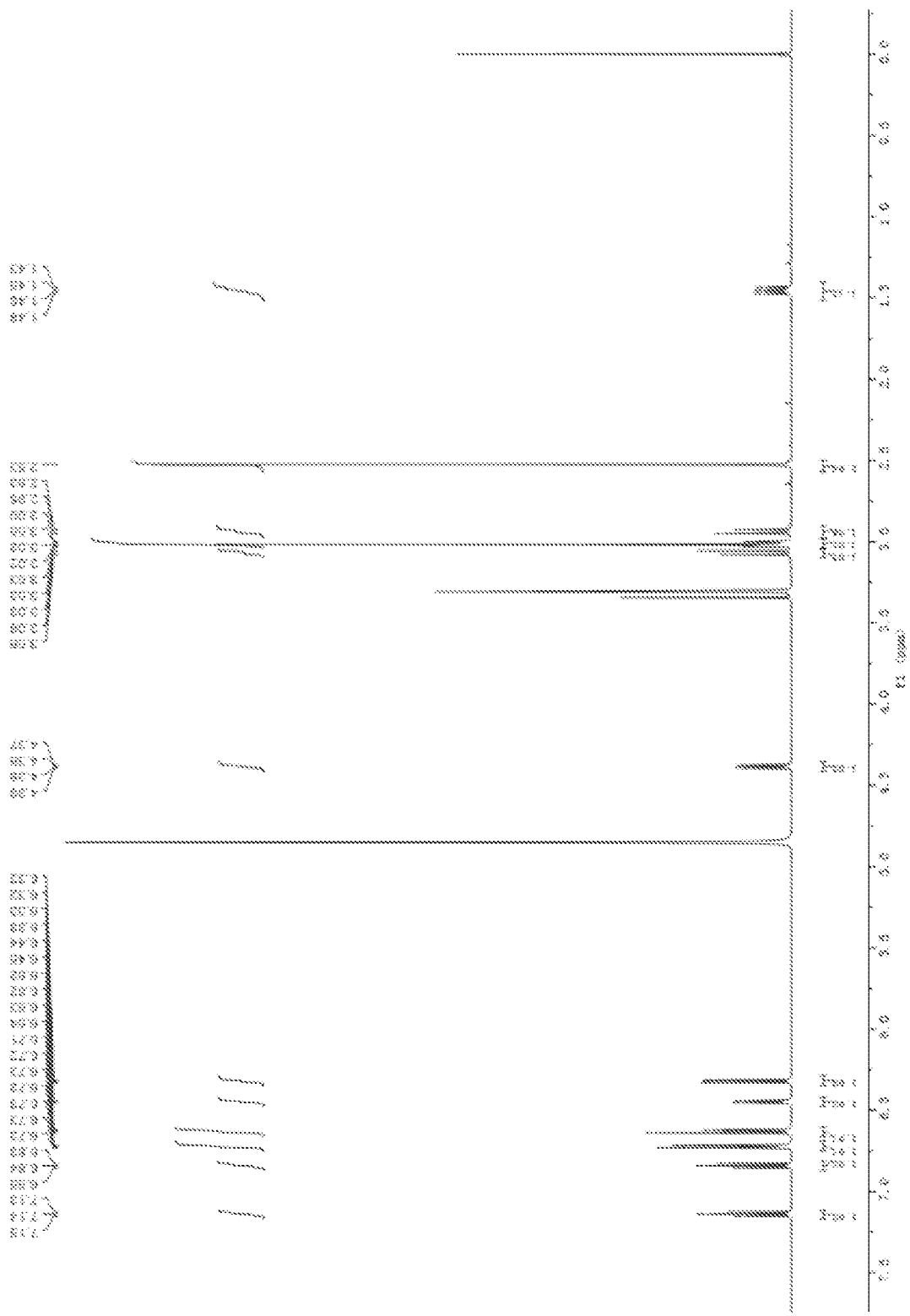
FIGS. 4A-4E show NMR spectra of 4-amino thaxtomin A.
Figure 4B:
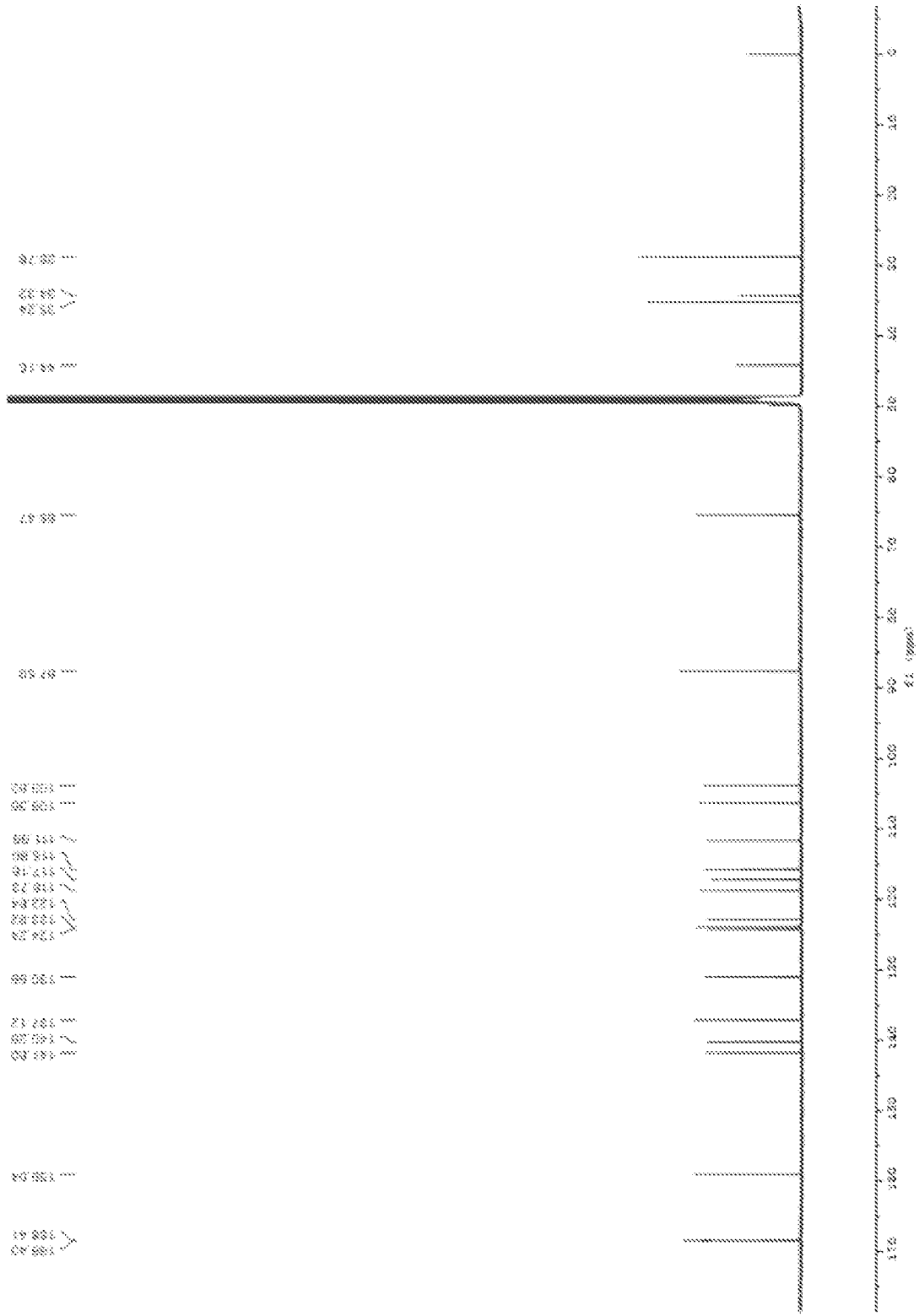
Figure 4C:
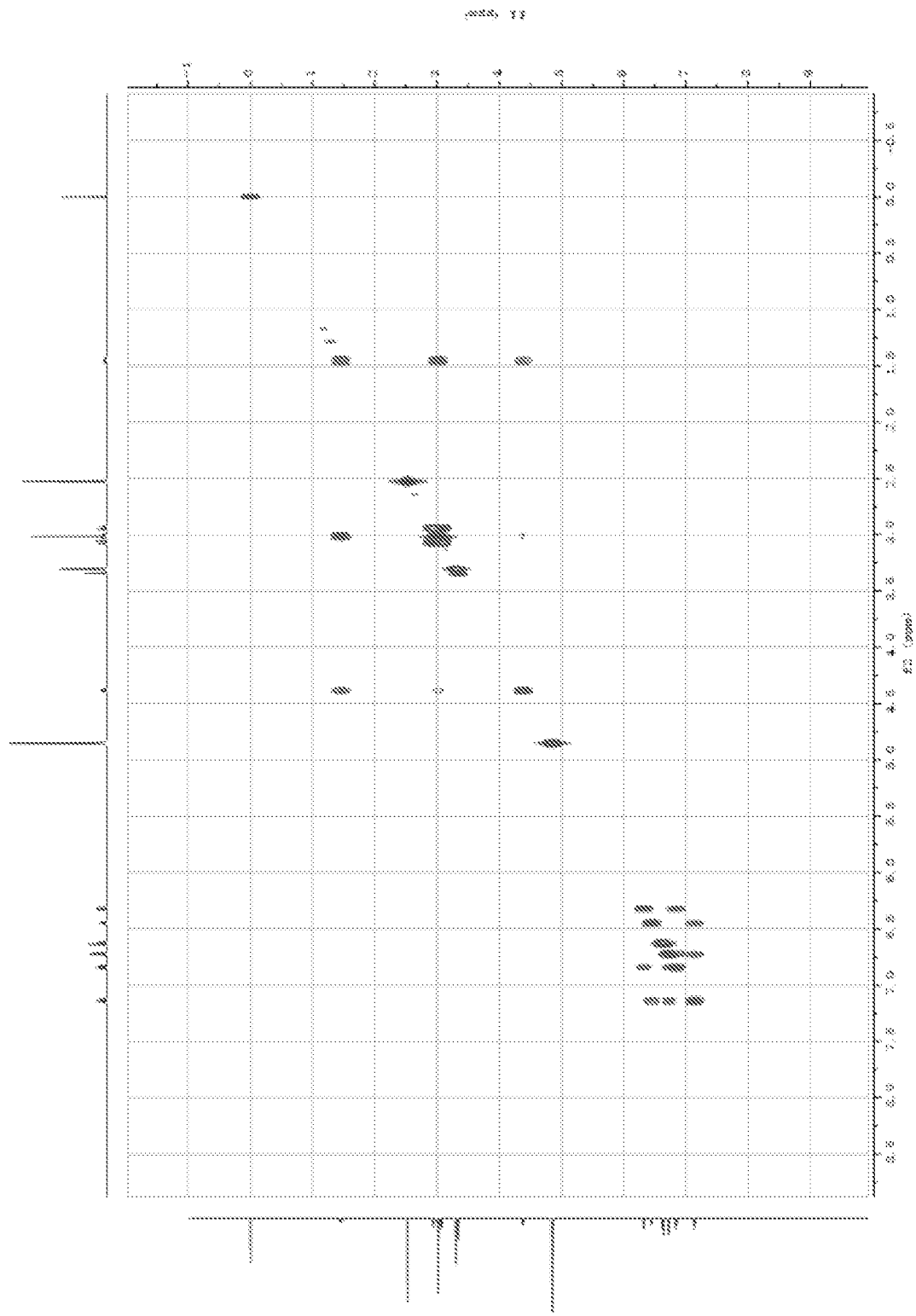
Figure 4D:
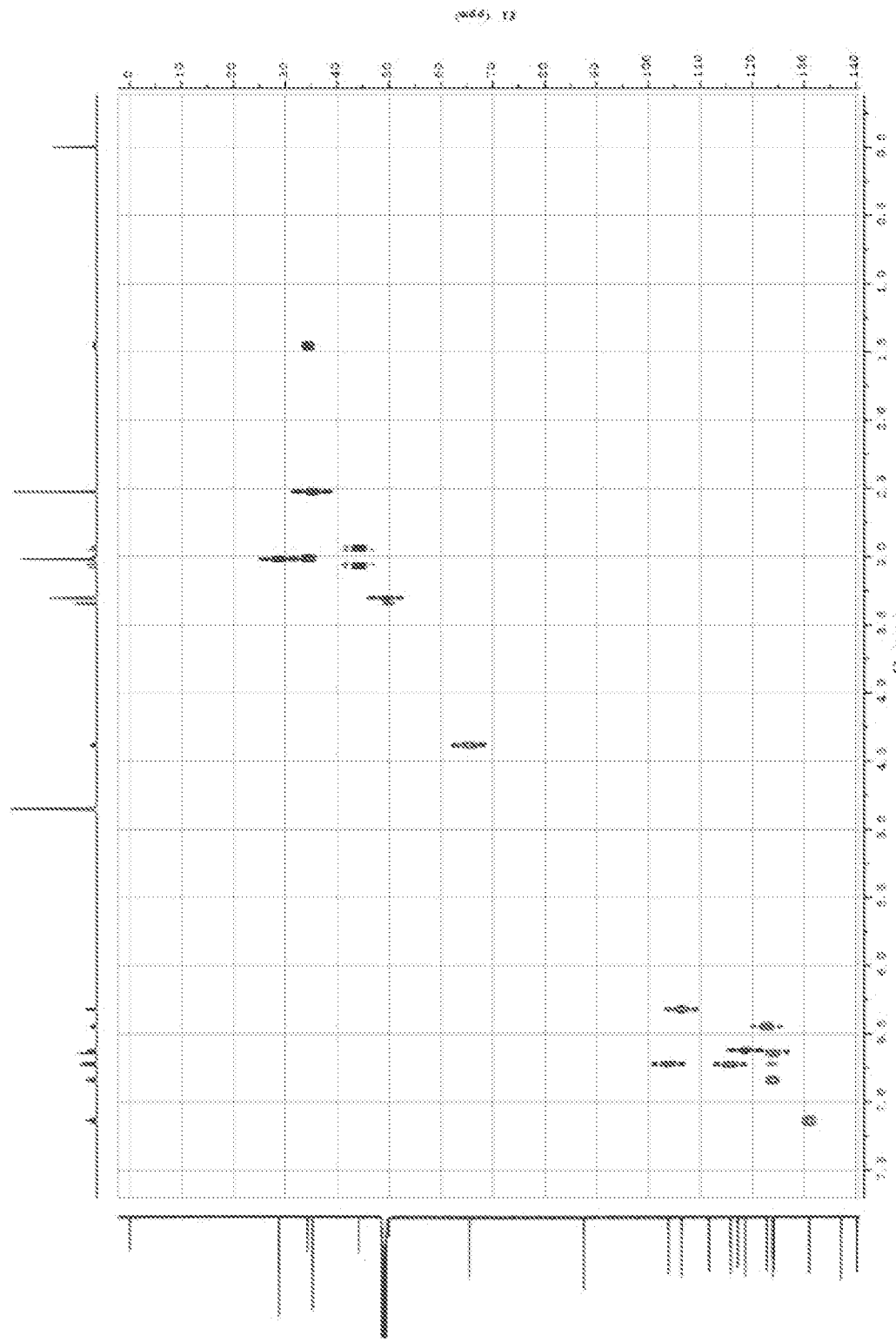
Figure 4E:
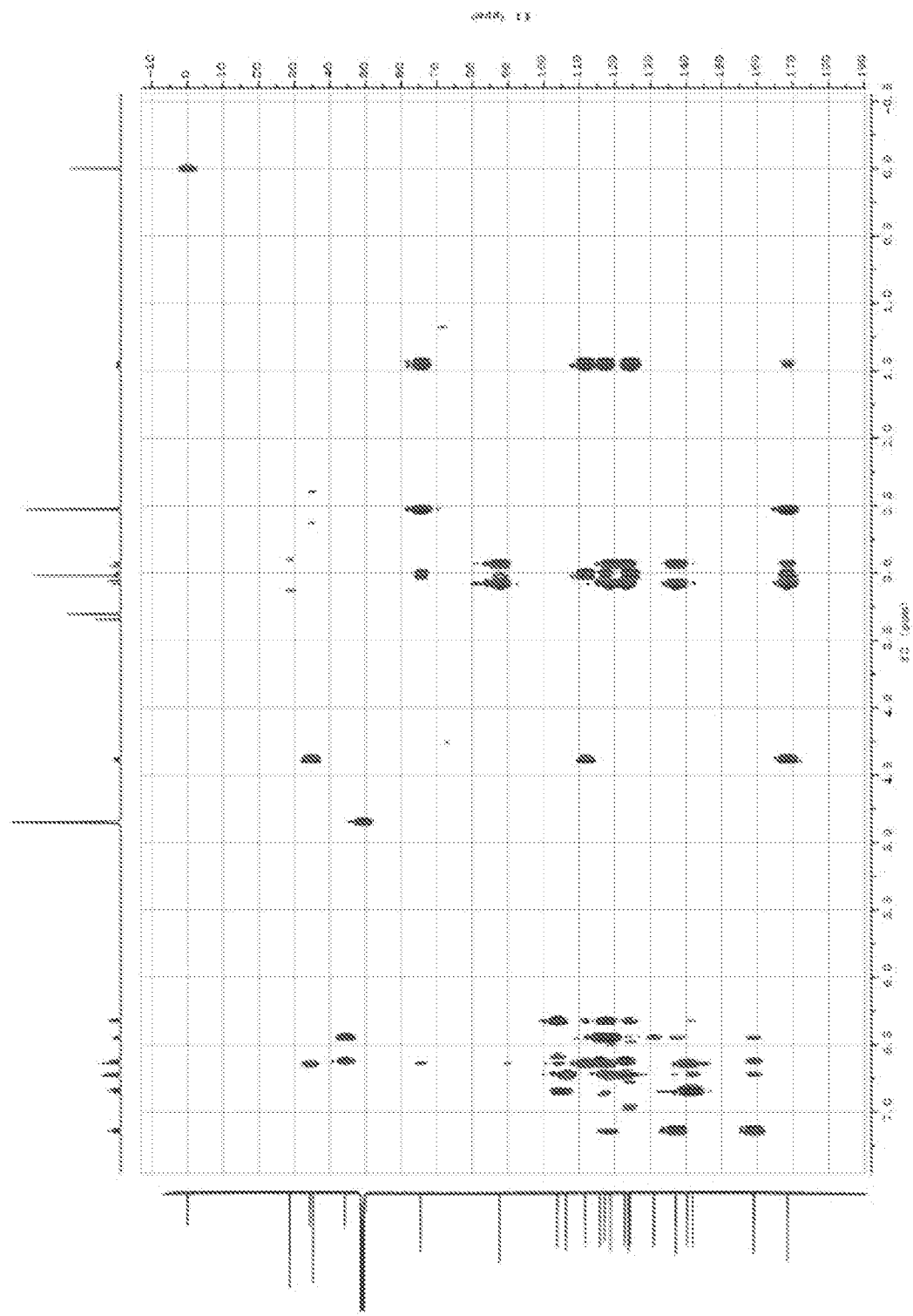

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the present disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

Materials

Molecular biology reagents and enzymes were purchased from Thermo Fisher Scientific, Inc. (Waltham, Massachusetts). Primers were ordered from Sigma-Aldrich, Inc. (Saint Louis, Missouri). NfsB DNA fragment was synthesized by Eurofins Scientific, Inc. (Lancaster, Pennsylvania). Thaxtomins were isolated according to previous methods using the engineered *S. albus* strain. Other chemicals and solvents were purchased from Sigma-Aldrich, Inc. or Thermo Fisher Scientific, Inc. DNA sequencing was performed at Eurofins Scientific, Inc. A Shimadzu Corporation (Kyoto, Japan) Prominence UHPLC systemfitted with an Agilent Poroshell 120 EC-C18 column (2.7 μm, 4.6×50 mm) coupled with a PDA detector was used for HPLC analysis. For semi-preparative HPLC isolation of compound 5, an Agilent ZORBAX RX-C18 column (5 μm, 4.6×250 mm) was used. NMR spectra of compound 5 were recorded in $CD_3OD$ on a Bruker Corporation (Billerica, Massachusetts) 600 MHz spectrometer at the University of Florida, Gainesville, FL, USA.

HPLC Methods

The HPLC column (Agilent Poroshell 120 EC-C18, 2.7 μm, 4.6×50 mm) was kept at 30° C. was eluted first with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 mL/min, and the products were detected at 380 nm or 280 nm with a PDA detector. For semi-preparative HPLC isolation of compound 5, the column (Agilent ZORBAX RX-C18, 5 μm, 4.6×250 mm) kept at 30° C. was eluted first with 25% solvent B (acetonitrile) for 9.5 min and then with a linear gradient of 25-99% solvent B for 1 min, followed by cleaning with 99% solvent B for 2.5 min. The column was then eluted with a linear gradient of 99-25% solvent B for 0.5 min and re-equilibrated with 25% solvent B for 0.5 min. The flow rate was set at 1 mL/min and the products were detected at 280 nm with a PDA detector. All isolates were combined, concentrated, freeze-dried, and then weighed.

LC-MS Analysis

A SHIMADZU Prominence UPLC system fitted with an Agilent Poroshell 120 EC-C18 column (2.7 μm, 4.6×50 mm) coupled with a Linear Ion Trap Quadrupole LC/MS/MS Mass Spectrometer system was used in the studies. The column was eluted with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 mL/min. For MS detection, turbo spray conditions were identical for all chemicals (curtain gas: 30 psi; ion spray voltage: 5500 V; temperature: 600° C.; ion source gas 1:50 psi; ion source gas 2:60 psi).

Radish Seedling Assay

Serial concentrations of thaxtomins in DMSO were added into 20 mL of 1.5% warm agar solution with gentle agitation to the final concentrations range from 0 to 2 μM. DMSO was included as a negative control. The solution was then poured into the plate for solidification at room temperature for 30 min. Radish seeds (W. Atlee Burpee & Co., Warminster Township, Pennsylvania) were surface disinfested, pregerminated, and selected when the radicle was 1+2 mm and just emerged from the seed coat. Six radish seedlings were equally located on the surface of each plate with the root ends all pointed in the same direction. Agar plates were covered and sealed with Parafilm®. The seedlings in the agar plates grew at room temperature under fluorescent lighting (12 h per day for 7 days), and then the seedling with average size of all seedlings in the same plate was selected for comparison.

Example 2: Preparation of Recombinant NfsB

The NfsB gene from *Haemophilus influenzae* (SEQ ID NO: 1) was synthesized and then amplified via PCR reaction by using a pair of primers, NfB-NdeI-F (SEQ ID NO: 2) and NfB-HindIII-R (SEQ ID NO: 3). The PCR product was purified and digested by the restriction enzymes NdeI and HindIII. The expression vector pET22b was also digested with NdeI and HindIII. Digested PCR product and plasmid were separated on agarose gel and corresponding bands were purified for the ligation to generate the expression construct pET22b-nfsB, which was sequenced to confirm successful ligation. *E. coli* BL21 GOLD transformation, protein expression, and purification followed previously established protocols. Briefly, *E. coli* cells harboring the expression constructs were cultured in Terrific broth medium supplemented with ampicillin at 37° C., 250 rpm. After $OD_{600}$ reached 0.6, protein expression was induced with isopropyl β-D-1-thiogalactopyranoside (IPTG; 0.1 mm) at 18° C., 190 rpm for 20 h. Cell pellets were then collected after centrifugation (5000 rpm, 10 min, and 4° C.). To purify recombinant proteins, cell pellets were resuspended in lysis buffer (cell biomass/volume=1:4; 25 mM Tris. HCl, PH 7.5, 100 mM NaCl, 10 mM imidazole, 3 mM β-mercaptoethanol, and 10% glycerol). Soluble proteins were released by sonication and collected by centrifugation at 18000 rpm at 4° C. for 40 min. Ni-NTA agarose resin (Thermo Fisher Scientific, Inc., Waltham, Massachusetts) was then used for protein purification. Purified recombinant proteins were exchanged into a storage buffer (25 mM Tris. HCl, pH 8.0, 50 mM NaCl, and 10% glycerol) by using a PD-10 column, aliquoted, and stored at −80° C. until use. Protein concentrations were determined by UV/Vis spectrophotometry using a NanoDrop Microvolume Spectrophotometer (Thermo Fisher Scientific, Inc., Waltham, Massachusetts). SDS-PAGE analysis indicated that the recombinant protein with a C-terminal His6 tag showed the expected size (26.7 kDa) (FIG. 2).

Example 3: Enzymatic Transformations of Thaxtomins into 4-Amino Thaxtomins

Activity of recombinant NfsB on thaxtomins A-D (FIG. 1) was evaluated. The reaction mixture (100 μL) included 50 mM Tris-HCl, pH 8.0, 2 mM NADPH, 500 μM FMN, and 2 mM substrate. Reactions were initiated by adding 135 μM NfsB and further incubated at 25° C., 400 rpm for 5 hours. All four thaxtomin analogs were partially transformed into new products which have no UV absorbance at 380 nm and are more polar in reverse-phase HPLC analysis (FIG. 3A), an indicator of the absence of the nitro group. Further LC-MS analysis revealed that the molecular weights of the products were 30 Da smaller than corresponding substrates (FIG. 3B), and agreed with the calculated molecular weights of 4-amino containing compounds 5-8 (FIG. 1).

Enzymatic reaction conditions were optimized with thaxtomin A as substrate. The enzyme showed the highest activity at 37° C. When coupled with a glucose dehydrogenase (GDH)- or phosphite dehydrogenase (PTDH)-based NADPH regeneration system, the enzyme at 10 μM achieved greater than 90% conversion of thaxtomin A (2 mM) at 37° C. in 8 hours. Furthermore, the clear cell lysates of *E. coli* BL21 strain expressing NfsB efficiently supported the nitro reduction reaction with thaxtomin A as substrate. In addition, a crude extract of engineered thaxtomin producing strain *Streptomyces albus*-thx2 was prepared; the extract contained about 69% thaxtomin A based on HPLC analysis. Recombinant NfsB and its clear cell lysates both completely converted thaxtomin A (1) in the crude extract into compound 5.

4-amino thaxtomin A (5): colorless solid; MS m/z 409.4 [M+H]+ (calcd. for $C_{22}H_{24}N_4O_4$, 409.2); $^1$H NMR (600 MHZ, $CD_3OD$) δ 7.14 (t, J=7.8 Hz, 1H), 6.84 (t, J=7.8 Hz, 1H), 6.75-6.69 (m, 2H), 6.66-6.60 (m, 2H), 6.45 (d, J=7.6 Hz, 1H), 6.32 (dd, J=7.4, 0.7 Hz, 1H), 4.38 (dd, J=9.2, 2.6 Hz, 1H), 3.07 (d, J=13.5 Hz, 1H), 3.04-2.98 (m, 4H), 2.94 (d, J=13.5 Hz, 1H), 2.53 (s, 3H), 1.45 (dd, J=15.4, 9.2 Hz, 1H). $^{13}$C NMR (150 MHZ, $CD_3OD$): ) δ 168.43, 168.41, 159.04, 141.80, 140.26, 137.12, 130.99, 124.24, 123.92, 122.84, 118.73, 117.18, 115.80, 111.66, 106.36, 103.82, 87.59, 65.47, 44.16, 35.24, 34.32, 28.78.

Example 4: Preparative Scale Synthesis of 4-Amino Thaxtomin A and Structure Characterization To further elucidate the chemical structures of products in the NfsB reaction, the reaction with NfsB containing *E. coli* cell lysates and the crude extract of thaxtomins as substrate was scaled up. In a 250 mL flask, the reaction mixture (100 mL) contained 7.5 mL of NfsB lysate (cell pellet from one liter TB culture generated 19 mL cell lysate), 2 mL crude extract of thaxtomins (21.9 mg/mL in DMSO, 69% of thaxtomin A), 5 mL of 50 mM Tris-HCl buffer at pH 8, 0.5 mL FMN (50 mM), 2 mL NADP+ (50 mM), 1 mL GDH (0.75 mM), 1.5 mL glucose (40%). The reaction was incubated at 37° C. for 6 hours and then terminated by adding the same volume of ethyl acetate. The products were extracted with ethyl acetate two additional times. The organic layers were combined, washed with water, dried and then evaporated in vacuo. The resulting residue was purified by HPLC and the fractions of targeted products were collected and dried by lyophilization to afford 15.5 mg of solid compound 5. The conversion yield was determined to be 55.6%. 1D and 2D NMR analysis of the isolated product revealed its structure as compound 5 (FIG. 1, FIGS. 4A-E, and Table 2).

TABLE 2

$^1$H and $^{13}$C NMR data comparison of compounds 1 and 5

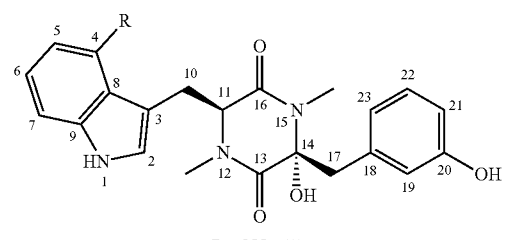

R = $NO_2$ (1)
R = $NH_2$ (5)

| | Thaxtomin A[a] | | 5[b] | |
|---|---|---|---|---|
| Position | $\delta_C$, type | $\delta_H$ (J in Hz) | $\delta_C$, type | $\delta_H$ (J in Hz) |
| 2 | 132.5, CH | 6.95, s | 124.2, CH | , 6.64, s |
| 3 | 110.5, C | | 111.7, C | |
| 4 | 143.6, C | | 141.8, C | |
| 5 | 119.2, CH | 7.84 (7.9, 1.0, dd) | 106.4, CH | 6.32 (7.4, 0.7, dd) |
| 6 | 121.0, CH | 7.19 (8.0, t) | 123.9, CH | 6.84, (7.8, t) |
| 7 | 118.6, CH | 7.68 (8.1, 1.0, dd) | 103.8, CH | 6.73, m |
| 8 | 119.8, C | | 117.2, C | |
| 9 | 141.1, C | | 140.3, C | |
| 10 | 33.5, $CH_2$ | 1.62 (14.2, 8.9, dd); 2.60 (14.1, 6.2,0.5, ddd) | 34.3, $CH_2$ | 1.45 (15.4, 9.2, dd); 3.01, m |
| 11 | 64.6, CH | 3.86 (8.9, 6.3, dd) | 65.5, CH | 4.38 (9.2, 2.6, dd) |

TABLE 2-continued

¹H and ¹³C NMR data comparison of compounds 1 and 5

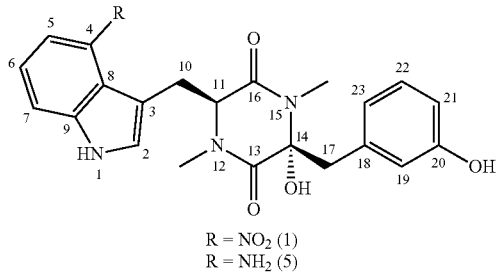

R = NO₂ (1)
R = NH₂ (5)

| Position | Thaxtomin A[a] $\delta_C$, type | $\delta_H$ (J in Hz) | 5[b] $\delta_C$, type | $\delta_H$ (J in Hz) |
|---|---|---|---|---|
| 13 | 168.3, C | | 168.4, C | |
| 14 | 88.0, C | | 87.6, C | |
| 16 | 166.8, C | | 168.4, C | |
| 17 | 45.4, $CH_2$ | 3.11 (13.4, d); 3.32 (13.5, d) | 44.2, $CH_2$ | 2.94 (13.5, d); 3.07 (13.5, d) |
| 18 | 137.4, C | | 137.1, C | |
| 19 | 118.4, CH | 6.71, m | 118.7, CH | 6.62, m |
| 20 | 159.1, C | | 159.0, C | |
| 21 | 115.8, CH | 6.71, m | 115.8, CH | 6.73, m |
| 22 | 131.2, CH | 7.23 (8.1, t) | 131.0, CH | 7.14 (7.8, t) |
| 23 | 122.7, CH | 6.71, m | 122.8, CH | 6.45 (7.6, t) |
| N-12 | 28.5, $CH_3$ | 3.03, s | 28.8, $CH_3$ | 3.02, s |
| N-15 | 34.2, $CH_3$ | 2.81, S | 35.2, $CH_3$ | 2.53, s |

[a]NMR data were reported in literature;
[b]NMR spectra were recorded in $CDOD_3$.

Example 5: Radish Seedling Assay of 4-Amino Thaxtomin A

Figure 5:
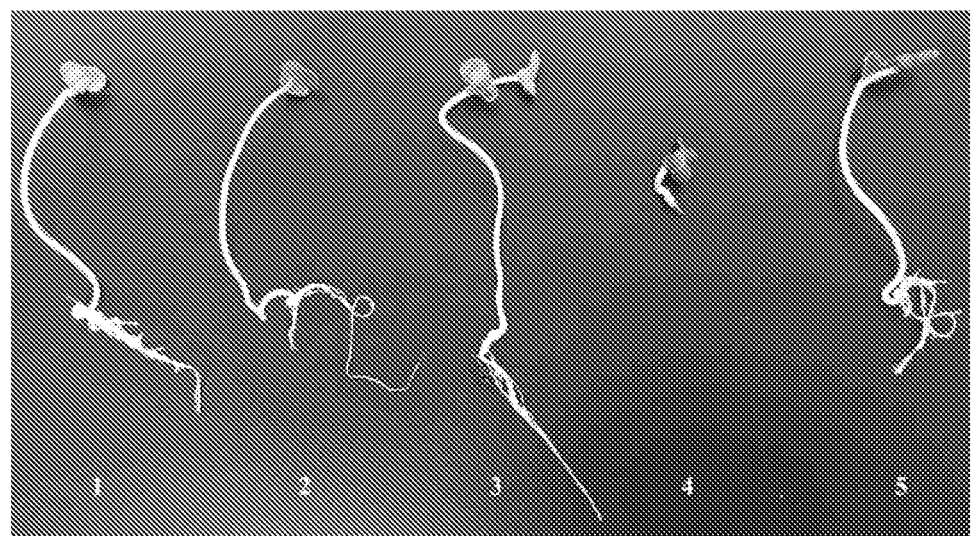
FIG. 5 shows radish seedling assay results. 1: DMSO; 2:2.0 µM 4-amino-thaxtomin A; 3:0.05 µM 4-amino-thaxtomin A; 4:2.0 µM thaxtomin A; 5:0.05 µM thaxtomin A.

A radish seedling assay was carried out to investigate the herbicidal activity of serial concentrations of 4-amino thaxtomin A (compound 5). The assay also included DMSO as negative control and thaxtomin A (1) as positive control. After seven days, the growth of radish seedlings on agar plate with compound 5 at both 0.05 μM and 2.0 μM was the same as the negative control DMSO (FIG. 5). Expectedly, thaxtomin A (1) significantly inhibited the growth of radish seedlings at 2.0 μM. The results indicated that compound 5 has minimal to no herbicidal activity to radish seedlings. The diminished herbicidal activity is caused by the transformation of the nitro group of thaxtomin A (1) into the amine group.

Example 6: Preparation of Recombinant NfsB R20A Mutant

The mutagenesis was done via overlapping PCR with four primers shown in Table 3. Briefly, the PCR reaction contained 2 μM of each primer, 0.1 mM of each dNTP (Thermo) and 0.5 μl Phusion high fidelity DNA polymerase (New England Biolabs, Inc., Ipswich, Massachussetts) in 1×GC reaction buffer. Reaction conditions consisted of an initial denaturation step at 98° C. for 30 s followed by 30 cycles of 98° C. for 10 s, 61° C. for 30 s, and 72° C. for 30 s, and a final extension of 72° C. for 5 min. The PCR product was separated on a 1% agarose gel, visualized by staining with SYBR™ Safe and extracted using a GeneJET Gel Extraction Kit (Thermo Fisher Scientific, Inc.). After gel purification and product concentration measurement, the purified PCR products were used for overlapping PCR. Equimolar amounts of purified fragments (around 100 ng) was added to a 25-μL PCR reaction. First, 15 PCR cycles were run without primers. Second, 2 μM end primers (nfsbFNdeI and nfsbRHindIII) were added to the reaction, which was then continued for 20 cycles. The PCR product was separated and purified on a 1% agarose gel. The purified product along with pET 22b was digested by NdeI and HindIII. The T4 ligation reaction was performed with a product and plasmid molar ratio at 3:1; 4° C. overnight. An aliquot (2 μl) was then used to transform 50 μl E. coli BL21-GOLD electro-competent cells and positive colonies were selected on the LB agar medium with 100 μg/ml ampicillin. The mutation was confirmed by sequencing the insert of the constructs isolated from positive colonies. The recombinant NfsB R20A mutant was prepared from E. coli BL21-GOLD following the same procedure in the preparation of the wild type.

TABLE 3

Primers used to prepare an NsfB R20A mutant

| Primer Name | Sequence (5' to 3') |
|---|---|
| nfsbFNdeI | ACTCATATGACTCAACTTACTCGTGAA (SEQ ID NO: 7) |
| nfsbRHindIII | ACTAAGCTTCCCCACCCATTTCACCACTTCA (SEQ ID NO: 8) |
| nfsbR20A-F | GCTCAACAGCGTATTACGACCC (SEQ ID NO: 9) |
| nfsbR20A-R | GGGTCGTAATACGCTGTTGAGC (SEQ ID NO: 10) |

Example 7: R20 is Catalytically Important in Converting Thaxtomins

Figure 7A:
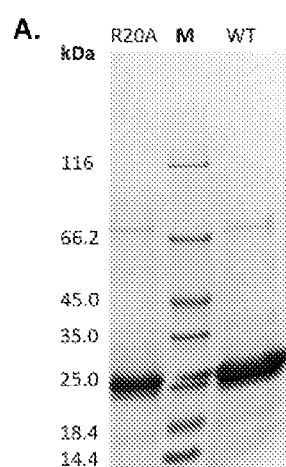
FIG. 7A shows SDS-PAGE analysis of purified recombinant wild type (WT) and NsfB R20A mutant. Both proteins showed the expected molecular weight at around 26 kDa.
Figure 7B:
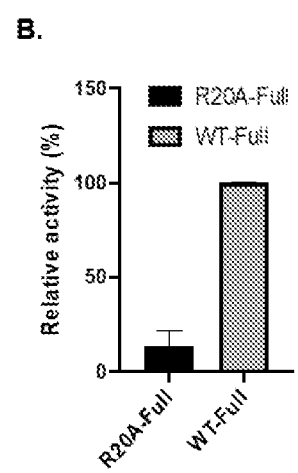
FIG. 7B shows the relative catalytic activity of wild type (WT) and NsfB R20A mutant in converting thaxtomin A under the same reaction conditions. The reaction product was analyzed by LC-MS analysis. The peak areas of amino-thaxtomine A produced in the WT-full reaction was set as 100% to normalize the relative activities of the mutant enzyme. The data represent the mean±standard deviation of at least two independent experiments.

Based on sequence alignments with homologs, it was further proposed that the relatively conserved R20 of NfsB may be catalytically critical by interacting with the nitro group of the substrate and potentially the cofactor FMN. A recombinant NfsB R20A mutant (FIG. 7A) was prepared in *E. coli* to test this hypothesis. The same concentrations of wild type NfsB and its R20A mutant A were incubated with 1 mM thaxtomin for 5 hours. LC-MS analysis revealed that the R20A mutant retained only about 12.5% of the catalytic activity of the wild type (FIG. 7B), indicating the catalytic role of R20 residue. The potential role of the R20 in the binding of cofactor FMN was further assessed. HPLC analysis identified that the FMN content of R20A mutant was about 42% of the wild type. Together, these results demonstrated that the R20 residue of NfsB is likely involved in the binding of both substrate and cofactor. Further mutagenesis of this and other residues potentially interacting with the substrate (e.g., A and B helices in FIG. 6) can likely develop NfsB mutants with improved activity and substrate specificity toward thaxtomins.

The present disclosure further includes the following aspects.

Aspect 1. A plant cell with stably integrated, recombinant DNA comprising a nucleotide sequence that encodes a nitroreductase protein.

Aspect 2. The plant cell of aspect 1, wherein the plant cell further comprises a heterologous promoter that is functional in plant cells and that is operably linked to the nucleotide sequence that encodes the nitroreductase protein.

Aspect 3. The plant cell of aspect 1 or 2, wherein the nucleotide sequence that encodes the nitroreductase protein is isolated from *Haemophilus influenzae, Actinobacillus indolicus, Avibacterium paragallinarum, Mannheimia succiniproducens, Staphylococcus arlettae, Actinobacillus succinogenes*, or *Arcobacter molloscorum.*

Aspect 4. The plant cell of aspect 3, wherein the nucleotide sequence that encodes the nitroreductase protein is isolated from *Haemophilus influenzae.*

Aspect 5. The plant cell of any of aspects 1-4, wherein the nitroreductase protein is NfsB.

Aspect 6. The plant cell of any of aspects 1-5, wherein the nucleotide sequence that encodes the nitroreductase protein comprises at least 90% sequence identity with SEQ ID NO: 1.

Aspect 7. The plant cell of any of aspects 1-5, wherein the nucleotide sequence that encodes the nitroreductase protein comprises at least 95% sequence identity with SEQ ID NO: 1.

Aspect 8. The plant cell of any of aspects 1-5, wherein the nucleotide sequence that encodes the nitroreductase protein comprises at least 97% sequence identity with SEQ ID NO: 1.

Aspect 9. The plant cell of any of aspects 1-5, wherein the nitroreductase protein comprises SEQ ID NO: 4.

Aspect 10. The plant cell of aspect 9, wherein the nitroreductase protein further comprises a portion comprising at least 70% sequence identity with SEQ ID NO: 5 and a portion comprising at least 70% sequence identity with SEQ ID NO: 6.

Aspect 11. The plant cell of aspect 9, wherein the nitroreductase protein further comprises a portion comprising at least 75% sequence identity with SEQ ID NO: 5 and a portion comprising at least 75% sequence identity with SEQ ID NO: 6.

Aspect 12. The plant cell of aspect 9, wherein the nitroreductase protein further comprises a portion comprising at least 80% sequence identity with SEQ ID NO: 5 and a portion comprising at least 80% sequence identity with SEQ ID NO: 6.

Aspect 13. The plant cell of aspect 9, wherein the nitroreductase protein further comprises a portion comprising at least 85% sequence identity with SEQ ID NO: 5 and a portion comprising at least 85% sequence identity with SEQ ID NO: 6.

Aspect 14. A transgenic plant comprising a plurality of the plant cell of any of aspects 1-13.

Aspect 15. A transgenic seed comprising a plurality of the plant cell of any of aspects 1-13.

Aspect 16. A transgenic plant callus comprising a plurality of the plant cell of any of aspects 1-13.

Aspect 17. A progeny plant grown from the seed of aspect 15 or the callus of aspect 16.

Aspect 18. The progeny plant of aspect 17, wherein the progeny plant comprises the nucleotide sequence that encodes a nitroreductase protein.

Aspect 19. The transgenic plant of aspect 14 or the progeny plant of 17, wherein the transgenic plant or progeny plant is a potato plant, a beet plant, a carrot plant, a parsnip plant, a radish plant, a rutabaga plant, a turnip plant, or a sweet potato plant.

Aspect 20. The transgenic plant or progeny plant of aspect 19, wherein the plant is a potato plant.

Aspect 21. A vegetable harvested from the plant of aspect 19 or 20.

Aspect 22. A plant chromosomal DNA segment comprising a recombinant polynucleotide flanked by native plant DNA, wherein the polynucleotide provides for expression of at least a nitroreductase protein.

Aspect 23. A plant chromosomal DNA segment comprising a recombinant DNA construct for expressing a nitroreductase protein comprising contiguous amino acids comprising at least 90% sequence identity to SEQ ID NO: 4.

Aspect 24. The plant chromosomal DNA segment of aspect 23, wherein the recombinant DNA construct for expressing a nitroreductase protein comprises contiguous amino acids comprising at least 95% sequence identity to SEQ ID NO: 4.

Aspect 25. The plant chromosomal DNA segment of aspect 23, wherein the recombinant DNA construct for expressing a nitroreductase protein comprises contiguous amino acids comprising at least 97% sequence identity to SEQ ID NO: 4.

Aspect 26. The plant chromosomal DNA segment of any of aspects 23-25, wherein the recombinant DNA construct for expressing a nitroreductase protein comprises a segment of contiguous amino acids comprising at least 70% sequence identity with SEQ ID NO: 5 and a segment of contiguous amino acids comprising at least 70% sequence identity with SEQ ID NO: 6.

Aspect 27. The plant chromosomal DNA segment of any of aspects 23-25, wherein the recombinant DNA construct for expressing a nitroreductase protein comprises a segment of contiguous amino acids comprising at least 75% sequence identity with SEQ ID NO: 5 and a segment of contiguous amino acids comprising at least 75% sequence identity with SEQ ID NO: 6.

Aspect 28. The plant chromosomal DNA segment of any of aspects 23-25, wherein the recombinant DNA construct for expressing a nitroreductase protein comprises a segment of contiguous amino acids comprising at least 80% sequence identity with SEQ ID NO: 5 and a segment of contiguous amino acids comprising at least 80% sequence identity with SEQ ID NO: 6.

Aspect 29. The plant chromosomal DNA segment of any of aspects 23-25, wherein the recombinant DNA construct for expressing a nitroreductase protein comprises a segment of contiguous amino acids comprising at least 85% sequence identity with SEQ ID NO: 5 and a segment of contiguous amino acids comprising at least 85% sequence identity with SEQ ID NO: 6.

Aspect 30. A transgenic plant cell comprising the plant chromosomal DNA segment of any of aspects 22-29.

Aspect 31. A method of improving resistance to at least one thaxtomin in a crop plant line comprising providing in the genome of the crop plant line the plant chromosomal DNA segment of any of aspects 22-29.

Aspect 32. The method of aspect 31, wherein the thaxtomin is secreted by a pathogenic microorganism.

Aspect 33. The method of aspect 32, wherein the pathogenic microorganism is *Streptomyces* scabies, *Streptomyces turgidiscabies*, *Streptomyces acidiscabies*, *Streptomyces luridiscabiei*, *Streptomyces puniciscabiei*, *Streptomyces nieviscabei*, *Streptomyces ipomoea*, or a combination thereof.

Aspect 34. The method of aspect 33, wherein the pathogenic microorganism is *Streptomyces* scabies.

Aspect 35. The method of aspect 31, wherein the thaxtomin is exogenously applied.

Aspect 36. The method of any of aspects 31-35, wherein the thaxtomin is thaxtomin A, thaxtomin B, thaxtomin C, thaxtomin D, or a combination thereof.

Aspect 37. The method of aspect 36, wherein the thaxtomin is thaxtomin A.

Aspect 38. A DNA construct comprising a nucleotide sequence encoding a nitroreductase protein.

Aspect 39. The DNA construct of aspect 38, wherein the DNA construct further comprises a heterologous promoter that is functional in plant cells and that is operably linked to the nucleotide sequence that encodes the nitroreductase protein.

Aspect 40. The DNA construct of aspect 38 or 39, wherein the nucleotide sequence that encodes the nitroreductase protein is isolated from *Haemophilus influenzae*, *Actinobacillus indolicus*, *Avibacterium paragallinarum*, *Mannheimia succiniproducens*, *Staphylococcus arlettae*, *Actinobacillus succinogenes*, or *Arcobacter molloscorum*.

Aspect 41. The DNA construct of aspect 40, wherein the nucleotide sequence that encodes the nitroreductase protein is isolated from *Haemophilus influenzae*.

Aspect 42. The DNA construct of any of aspects 38-41, wherein the nitroreductase protein is NfsB.

Aspect 43. The DNA construct of any of aspects 38-42, wherein the nucleotide sequence that encodes the nitroreductase protein comprises at least 90% sequence identity with SEQ ID NO: 1.

Aspect 44. The DNA construct of any of aspects 38-42, wherein the nucleotide sequence that encodes the nitroreductase protein comprises at least 95% sequence identity with SEQ ID NO: 1.

Aspect 45. The DNA construct of any of aspects 38-42, wherein the nucleotide sequence that encodes the nitroreductase protein comprises at least 97% sequence identity with SEQ ID NO: 1.

Aspect 46. The DNA construct of any of aspects 38-42, wherein the nitroreductase protein comprises SEQ ID NO: 4.

Aspect 47. The DNA construct of aspect 46, wherein the nitroreductase protein further comprises a portion comprising at least 70% sequence identity with SEQ ID NO: 5 and a portion comprising at least 70% sequence identity with SEQ ID NO: 6.

Aspect 48. The DNA construct of aspect 46, wherein the nitroreductase protein further comprises a portion comprising at least 75% sequence identity with SEQ ID NO: 5 and a portion comprising at least 75% sequence identity with SEQ ID NO: 6.

Aspect 49. The DNA construct of aspect 46, wherein the nitroreductase protein further comprises a portion comprising at least 80% sequence identity with SEQ ID NO: 5 and a portion comprising at least 80% sequence identity with SEQ ID NO: 6.

Aspect 50. The DNA construct of aspect 46, wherein the nitroreductase protein further comprises a portion comprising at least 85% sequence identity with SEQ ID NO: 5 and a portion comprising at least 85% sequence identity with SEQ ID NO: 6.

Aspect 51. An expression cassette comprising the DNA construct of any of aspects 38-50.

Aspect 52. The expression cassette of aspect 51, wherein the nucleotide sequence is operably linked to a heterologous promoter.

Aspect 53. A host cell comprising the DNA construct of any of aspects 38-45 or the expression cassette of aspect 51 or 52.

Aspect 54. The host cell of aspect 53, wherein the host cell is a bacterial cell.

Aspect 55. The host cell of aspect 53 or 54, wherein the host cell comprises the expression cassette of aspect 51 or 52.

Aspect 56. A plant cell having stably incorporated into its genome a heterologous polynucleotide comprising a nucleotide sequence encoding a nitroreductase protein, wherein the heterologous polynucleotide comprises a nucleotide sequence comprising at least 90% sequence identity to SEQ ID NO: 1 or a variant or fragment thereof; wherein the nucleotide sequence encoding the nitroreductase protein, when transcribed and translated, produces a protein capable of reducing a nitro group on a thaxtomin.

Aspect 57. The plant cell of aspect 56, wherein the heterologous polynucleotide comprises a nucleotide sequence comprising at least 95% sequence identity to SEQ ID NO: 1 or a variant or fragment thereof; wherein the nucleotide sequence encoding the nitroreductase protein, when transcribed and translated, produces a protein capable of reducing a nitro group on a thaxtomin.

Aspect 58. The plant cell of aspect 56, wherein the heterologous polynucleotide comprises a nucleotide sequence comprising at least 97% sequence identity to SEQ ID NO: 1 or a variant or fragment thereof; wherein the nucleotide sequence encoding the nitroreductase protein, when transcribed and translated, produces a protein capable of reducing a nitro group on a thaxtomin.

Aspect 59. The plant cell of any of aspects 56-58, wherein the nitroreductase protein comprises SEQ ID NO: 4.

Aspect 60. The plant cell of aspect 59, wherein the nitroreductase protein further comprises a portion comprising at least 70% sequence identity with SEQ ID NO: 5 and a portion comprising at least 70% sequence identity with SEQ ID NO: 6.

Aspect 61. The plant cell of aspect 59, wherein the nitroreductase protein further comprises a portion comprising at least 75% sequence identity with SEQ ID NO: 5 and a portion comprising at least 75% sequence identity with SEQ ID NO: 6.

Aspect 62. The plant cell of aspect 59, wherein the nitroreductase protein further comprises a portion comprising at least 80% sequence identity with SEQ ID NO: 5 and a portion comprising at least 80% sequence identity with SEQ ID NO: 6.

Aspect 63. The plant cell of aspect 59, wherein the nitroreductase protein further comprises a portion comprising at least 85% sequence identity with SEQ ID NO: 5 and a portion comprising at least 85% sequence identity with SEQ ID NO: 6.

Aspect 64. The plant cell of any of aspects 56-63, wherein the thaxtomin is secreted by *Streptomyces scabies, Streptomyces turgidiscabies, Streptomyces acidiscabies, Streptomyces luridiscabiei, Streptomyces puniciscabiei, Streptomyces nieviscabei, Streptomyces ipomoea*, or a combination thereof.

Aspect 65. The plant cell of aspect 64, wherein the thaxtomin is secreted by *Streptomyces scabies*.

Aspect 66. The plant cell of any of aspects 56-63, wherein the thaxtomin is exogenously applied as a component of an agricultural composition.

Aspect 67. The plant cell of aspect 66, wherein the agricultural composition is an herbicide.

Aspect 68. The plant cell of any of aspects 56-63, wherein the plant cell comprises the expression cassette of aspect 51 or 52.

Aspect 69. The plant cell of any of aspects 56-63, wherein the nucleotide sequence encoding a nitroreductase protein is operably linked to a heterologous promoter.

Aspect 70. The plant cell of any of aspects 56-69, wherein the plant cell is from a dicot.

Aspect 71. The plant cell of aspect 70, wherein the dicot is a potato plant, a beet plant, a carrot plant, a parsnip plant, a radish plant, a rutabaga plant, a turnip plant, or a sweet potato plant.

Aspect 72. A plant or plant part comprising the plant cell of any of aspects 56-63.

Aspect 73. A transgenic seed from the plant of aspect 72.

Aspect 74. A method for reducing plant damage due to a plant pathogenic organism comprising providing to a plant or soil before or after introduction of a seed, bulb, tuber, bud, stem, corm, plant part, or a plant, a composition comprising the DNA construct of any of aspects 38-50, the expression cassette of aspect 51 or 52, or the host cell of any of aspects 53-55.

Aspect 75. A method for reducing the damage caused by common scab of potato to the roots of a plant comprising providing to a plant or soil before or after introduction of a seed, bulb, tuber, bud, stem, corm, plant part, or a plant, a composition comprising the DNA construct of any of aspects 38-50, the expression cassette of aspect 51 or 52, or the host cell of any of aspects 53-55.

Aspect 76. A method for reducing the damage caused by a thaxtomin to the roots of a plant comprising providing to a plant or soil before or after introduction of a seed, bulb, tuber, bud, stem, corm, plant part, or a plant, a composition comprising the DNA construct of any of aspects 38-50, the expression cassette of aspect 51 or 52, or the host cell of any of aspects 53-55.

It should be emphasized that the above-described embodiments of the present disclosure are merely possible examples of implementations set forth for a clear understanding of the principles of the present disclosure. Many variations and modifications may be made to the above-described embodiment(s) without departing substantially from the spirit and principles of the present disclosure. All such modifications and variations are intended to be included herein within the scope of this disclosure and protected by the following claims.

REFERENCES

1. Savary, S.; Willocquet, L.; Pethybridge, S. J.; Esker, P.; McRoberts, N.; Nelson, A., The global burden of pathogens and pests on major food crops. *Nat Ecol Evol* 2019, 3 (3), 430-439.
2. Ogbeide, O.; Tongo, I.; Ezemonye, L., Assessing the distribution and human health risk of organochlorine pesticide residues in sediments from selected rivers. *Chemosphere* 2016, 144, 1319-1326.
3. Rodriguez, C.; Taylor, P.; Devine, B.; Van Buynder, P.; Weinstein, P.; Cook, A., Assessing Health Risks from Pesticides in Recycled Water: A Case Study of Augmentation of Drinking Water Supplies in Perth, Western Australia. *Hum Ecol Risk Assess* 2012, 18 (6), 1216-1236.
4. Marble, S. C.; Koeser, A. K.; Hasing, G., A Review of Weed Control Practices in Landscape Planting Beds: Part II-Chemical Weed Control Methods. *Hortscience* 2015, 50 (6), 857-862.
5. Frazier, M. T.; Mullin, C. A.; Frazier, J. L.; Ashcraft, S. A.; Leslie, T. W.; Mussen, E. C.; Drummond, F. A., Assessing Honey Bee (Hymenoptera: Apidae) Foraging Populations and the Potential Impact of Pesticides on Eight US Crops. *J Econ Entomol* 2015, 108 (5), 2141-2152.
6. Peterson, M. A.; Collavo, A.; Ovejero, R.; Shivrain, V.; Walsh, M. J., The challenge of herbicide resistance around the world: a current summary. *Pest Manag Sci* 2018, 74 (10), 2246-2259.
7. Lorsbach, B. A.; Sparks, T. C.; Cicchillo, R. M.; Garizi, N. V.; Hahn, D. R.; Meyer, K. G., Natural products: a strategic lead generation approach in crop protection discovery. *Pest Manag Sci* 2019, 75 (9), 2301-2309.
8. Dayan, F. E.; Cantrell, C. L.; Duke, S. O., Natural products in crop protection. *Bioorg Med Chem* 2009, 17 (12), 4022-4034.
9. van Esse, H. P.; Reuber, T. L.; van der Does, D., Genetic modification to improve disease resistance in crops. *New Phytol* 2019. doi: 10.1111/nph. 15967
10. Funke, T.; Han, H.; Healy-Fried, M. L.; Fischer, M.; Schonbrunn, E., Molecular basis for the herbicide resistance of Roundup Ready crops. *Proc Natl Acad Sci USA* 2006, 103 (35), 13010-13015.
11. Loria, R.; Kers, J. A.; Joshi, M. V.; Johnson, E. G., Evolution of plant pathogenicity in the genus *Streptomyces. Phytopathology* 2004, 94 (6), S123-S123.
12. Loria, R.; Kers, J.; Joshi, M., Evolution of plant pathogenicity in *Streptomyces. Annu Rev Phytopathol* 2006, 44, 469-487.
13. Zhang, Y.; Bignell, D.; Zuo, R.; Fan, Q.; Huguet-Tapia, J.; Ding, Y.; Loria, R., Evolution of plant pathogenicity in *Streptomyces. Phytopathology* 2016, 106 (12), 173-174.
14. Fry, B. A.; Loria, R., Thaxtomin A: evidence for a plant cell wall target. *Physiol Mol Plant P* 2002, 60 (1), 1-8.
15. Lapwood, D. H.; Wellings, L. W.; Hawkins, J. H., Irrigation as a Practical Means to Control Potato Common Scab (*Streptomyces*-Scabies). *Plant Pathol* 1971, 20 (4), 157-163.
16. King, R. R.; Lawrence, C. H.; Clark, M. C.; Calhoun, L. A., Isolation and Characterization of Phytotoxins Associated with *Streptomyces* Scabies. *J Chem Soc Chem Comm* 1989, (13), 849-850.
17. King, R. R.; Lawrence, C. H.; Clark, M. C., Correlation of Phytotoxin Production with Pathogenicity of *Streptomyces*-Scabies Isolates from Scab Infected Potato-Tubers. *Am Potato J* 1991, 68 (10), 675-680.

18. Babcock, M. J.; Eckwall, E. C.; Schottel, J. L., Production and Regulation of Potato-Scab-Inducing Phytotoxins by *Streptomyces*-Scabies. *J Gen Microbiol* 1993, 139, 1579-1586.
19. Lawrence, C. H.; Clark, M. C.; King, R. R., Induction of Common Scab Symptoms in Aseptically Cultured Potato-Tubers by the Vivotoxin, Thaxtomin. *Phytopathology* 1990, 80 (7), 606-608.
20. Wilson, C. R.; Luckman, G. A.; Tegg, R. S.; Yuan, Z. Q.; Wilson, A. J.; Eyles, A.; Conner, A. J., Enhanced resistance to common scab of potato through somatic cell selection in cv. Iwa with the phytotoxin thaxtomin A. *Plant Pathol* 2009, 58 (1), 137-144.
21. Thompson, H. K.; Tegg, R. S.; Corkrey, R.; Wilson, C. R., Optimal rates of 2,4-dichlophenoxyacetic acid foliar application for control of common scab in potato. *Ann Appl Biol* 2014, 165 (2), 293-302.
22. St-Onge, R.; Gadkar, V. J.; Arseneault, T.; Goyer, C.; Filion, M., The ability of *Pseudomonas* sp. LBUM 223 to produce phenazine-1-carboxylic acid affects the growth of *Streptomyces* scabies, the expression of thaxtomin biosynthesis genes and the biological control potential against common scab of potato. *Fems Microbiol Ecol* 2011, 75 (1), 173-183.
23. Arseneault, T.; Pieterse, C. M. J.; Gerin-Ouellet, M.; Goyer, C.; Filion, M., Long-Term Induction of Defense Gene Expression in Potato by *Pseudomonas* sp LBUM223 and *Streptomyces* scabies. *Phytopathology* 2014, 104 (9), 926-932.
24. Arseneault, T.; Goyer, C.; Filion, M., *Pseudomonas fluorescens* LBUM223 Increases Potato Yield and Reduces Common Scab Symptoms in the Field. *Phytopathology* 2015, 105 (10), 1311-1317.
25. Li, B. Y.; Wang, B.; Pan, P.; Li, P. G.; Qi, Z. G.; Zhang, Q. Y.; Shi, C. Y.; Hao, W. S.; Zhou, B.; Lin, R. S., *Bacillus altitudinis* strain AMCC 101304: a novel potential biocontrol agent for potato common scab. *Biocontrol Sci Techn* 2019.
26. Meng, Q. X.; Jiang, H. H.; Hanson, L. E.; Hao, J. J., Characterizing a novel strain of *Bacillus amyloliquefaciens* BAC03 for potential biological control application. *J Appl Microbiol* 2012, 113 (5), 1165-1175.
27. Meng, Q. X.; Hanson, L. E.; Douches, D.; Hao, J. J. J., Managing scab diseases of potato and radish caused by *Streptomyces* spp. using *Bacillus amyloliquefaciens* BAC03 and other biomaterials. *Biol Control* 2013, 67 (3), 373-379.
28. Jiang, H.; Meng, Q.; Hao, J., Optimization of *Bacillus amyloliquefaciens* BAC03 application in controlling *Streptomyces* scabies. *Phytopathology* 2015, 105 (11), 65-65.
29. Jiang, H.; Meng, Q.; Hao, J., Potentials and mechanisms of *Bacillus amyloliquefaciens* BAC03 in plant disease control. *Phytopathology* 2014, 104 (3), 3-3.
30. Sarwar, A.; Latif, Z.; Zhang, S. Y.; Zhu, J.; Zechel, D. L.; Bechthold, A., Biological Control of Potato Common Scab With Rare Isatropolone C Compound Produced by Plant Growth Promoting *Streptomyces* A1RT. *Front Microbiol* 2018, 9:1126. doi: 10.3389/fmicb.2018.01126.
31. Sarwar, A.; Latif, Z.; Zhang, S. Y.; Hao, J. J.; Bechthold, A., A Potential Biocontrol Agent *Streptomyces violaceusniger* AC12AB for Managing Potato Common Scab. *Front Microbiol* 2019, 10:202. doi: 10.3389/fmicb.2019.00202.
32. Braun, S.; Gevens, A.; Charkowski, A.; Allen, C.; Jansky, S., Potato Common Scab: a Review of the Causal Pathogens, Management Practices, Varietal Resistance Screening Methods, and Host Resistance. *Am J Potato Res* 2017, 94 (4), 283-296.
33. Jiang, G. D.; Zuo, R.; Zhang, Y.; Powell, M. M.; Zhang, P. L.; Hylton, S. M.; Loria, R.; Ding, Y. S., One-Pot Biocombinatorial Synthesis of Herbicidal Thaxtomins. *Acs Catal* 2018, 8 (11), 10761-10768.
34. Zhang, H. B.; Wang, Q. P.; Ning, X.; Hang, H.; Ma, J.; Yang, X. D.; Lu, X. L.; Zhang, J. B.; Li, Y. H.; Niu, C. W.; Song, H. R.; Wang, X.; Wang, P. G., Synthesis and Biological Evaluations of a Series of Thaxtomin Analogues. *J Agr Food Chem* 2015, 63 (14), 3734-3741.
35. Orlandi, M.; Brenna, D.; Harms, R.; Jost, S.; Benaglia, M., Recent Developments in the Reduction of Aromatic and Aliphatic Nitro Compounds to Amines. *Org Process Res Dev* 2018, 22 (4), 430-445.
36. Akiva, E.; Copp, J. N.; Tokuriki, N.; Babbitt, P. C., Evolutionary and molecular foundations of multiple contemporary functions of the nitroreductase superfamily. *Proc Natl Acad Sci USA* 2017, 114 (45), E9549-E9558.
37. Roldan, M. D.; Perez-Reinado, E.; Castillo, F.; Moreno-Vivian, C., Reduction of polynitroaromatic compounds: the bacterial nitroreductases. *FEMS Microbiol Rev* 2008, 32 (3), 474-500.
38. Zenno, S.; Koike, H.; Kumar, A. N.; Jayaraman, R.; Tanokura, M.; Saigo, K., Biochemical characterization of NfsA, the *Escherichia coli* major nitroreductase exhibiting a high amino acid sequence homology to Frp, a *Vibrio harveyi* flavin oxidoreductase. *J Bacteriol* 1996, 178 (15), 4508-4514.
39. Zenno, S.; Koike, H.; Tanokura, M.; Saigo, K., Gene cloning, purification, and characterization of NfsB, a minor oxygen-insensitive nitroreductase from *Escherichia coli*, similar in biochemical properties to FRase I, the major flavin reductase in *Vibrio fischeri*. *J Biochem* 1996, 120 (4), 736-744.
40. Rau, J.; Stolz, A., Oxygen-insensitive nitroreductases NfsA and NfsB of *Escherichia coli* function under anaerobic conditions as lawsone-dependent azo reductases. *Appl Environ Microb* 2003, 69 (6), 3448-3455.
41. Smith, A. L.; Erwin, A. L.; Kline, T.; Unrath, W. C. T.; Nelson, K.; Weber, A.; Howald, W. N., Chloramphenicol is a substrate for a novel nitroreductase pathway in *Haemophilus influenzae*. *Antimicrob Agents Ch* 2007, 51 (8), 2820-2829.
42. LinWu, S. W.; Syu, C. J.; Chen, Y. L.; Wang, A. H. J.; Peng, F. C., Characterization of *Escherichia coli* nitroreductase NfsB in the metabolism of nitrobenzodiazepines. *Biochem Pharmacol* 2009, 78 (1), 96-103.
43. Yanto, Y.; Hall, M.; Bommarius, A. S., Nitroreductase from *Salmonella typhimurium*: characterization and catalytic activity. *Org Biomol Chem* 2010, 8 (8), 1826-1832.
44. Akiva, E.; Copp, J. N.; Tokuriki, N.; Babbitt, P. C., Evolutionary and molecular foundations of multiple contemporary functions of the nitroreductase superfamily. *P Natl Acad Sci USA* 2017, 114 (45), E9549-E9558.
45. Crofts, T. S.; Sontha, P.; King, A. O.; Wang, B.; Biddy, B. A.; Zanolli, N.; Gaumnitz, J.; Dantas, G., Discovery and Characterization of a Nitroreductase Capable of Conferring Bacterial Resistance to Chloramphenicol. *Cell Chem Biol* 2019, 26 (4), 559-570.
46. Green, K. D.; Fosso, M. Y.; Mayhoub, A. S.; Garneau-Tsodikova, S., Investigating the promiscuity of the chloramphenicol nitroreductase from *Haemophilus influenzae* towards the reduction of 4-nitrobenzene derivatives. *Bioorg Med Chem Lett* 2019, 29 (9), 1127-1132.

47. Doumbou, C. L.; Akimov, V.; Beaulieu, C., Selection and characterization of microorganisms utilizing thaxtomin A, a phytotoxin produced by *Streptomyces* scabies. *Appl Environ Microb* 1998, 64 (11), 4313-4316.

48. King, R. R.; Lawrence, C. H.; Calhoun, L. A., Chemistry of Phytotoxins Associated with *Streptomyces*-Scabies, the Causal Organism of Potato Common Scab. *J Agr Food Chem* 1992, 40 (5), 834-837.

What is claimed is:

1. A method of improving resistance to at least one thaxtomin in a crop plant line, the method comprising:

providing in the genome of the crop plant line a plant chromosomal DNA segment comprising a recombinant polynucleotide flanked by native plant DNA;

wherein the crop plant line has improved resistance to at least one thaxtomin compared to a control crop plant line without the recombinant polynucleotide;

wherein the recombinant polynucleotide encodes a nitroreductase protein capable of reducing a nitro group of the at least one thaxtomin;

wherein the recombinant polynucleotide sequence is SEQ ID NO: 1; or wherein the recombinant polynucleotide encodes the *Haemophilus influenzae* NfsB protein of SEQ ID NO: 4;

wherein the at least one thaxtomin is selected from thaxtomin A, thaxtomin B, thaxtomin C, and thaxtomin D, or a combination thereof;

wherein the at least one thaxtomin is secreted by a microorganism; and wherein the at least one thaxtomin secreted by the microorganism is an exogenously applied thaxtomin.

2. The method of claim 1, wherein the microorganism is *Streptomyces scabies, Streptomyces turgidiscabies, Streptomyces acidiscabies, Streptomyces luridiscabiei, Streptomyces puniciscabiei, Streptomyces nieviscabei, Streptomyces ipomoea*, or a combination thereof.

* * * * *

SEQUENCE LISTING

```
<160> NUMBER OF SEQ ID NOS: 10

<210> SEQ ID NO 1
<211> LENGTH: 663
<212> TYPE: DNA
<213> ORGANISM: Haemophilus influenzae

<400> SEQUENCE: 1
atgactcaac ttactcgtga acaagttctt gaactcttcc atcaacgcag ctcaacacgt      60
tattacgacc caacaaaaaa aatcagtgat gaagattttg aatgtatttt agagtgcggt     120
cgattatcgc cgagttctgt aggctctgag ccttggaaat ttttagtgat tcaaaataaa     180
accttacgcg aaaaaatgaa acctttagc tggggaatga taaatcagct tgataattgc      240
agtcatcttg tggtaattct cgcgaagaaa aatgcccgtt atgatagtcc gttttttgtg     300
gatgtgatgg cacgcaaagg cttgaacgca gagcaacaac aagccgccct cacaaaatac     360
aaagccctgc aagaagaaga tatgaaatta ctcgaaaacg accgcacttt atttgattgg     420
tgcagcaaac aaacttatat cgcccttgca aatatgctta ctggagcttc agcccttggc     480
atcgactctt gcccaattga aggttttcat tacgacaaaa tgaatgaatg cctcgccgaa     540
gaaggattat tcgatcctca agaatatgcg gtttctgtcg ccgcaaccct tggctatcgc     600
tcacgcgata ttgcgaaaaa atcccgtaaa ggattggatg aagtggtgaa atgggtgggg     660
taa                                                                     663

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
actcatatga ctcaacttac tcgtgaa                                           27

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
actaagcttc cccacccatt tcaccacttc a                                      31

<210> SEQ ID NO 4
<211> LENGTH: 220
<212> TYPE: PRT
<213> ORGANISM: Haemophilus influenzae

<400> SEQUENCE: 4

Met Thr Gln Leu Thr Arg Glu Gln Val Leu Glu Leu Phe His Gln Arg
1               5                   10                  15

Ser Ser Thr Arg Tyr Tyr Asp Pro Thr Lys Lys Ile Ser Asp Glu Asp
            20                  25                  30

Phe Glu Cys Ile Leu Glu Cys Gly Arg Leu Ser Pro Ser Ser Val Gly
```

```
                35                  40                  45
Ser Glu Pro Trp Lys Phe Leu Val Ile Gln Asn Lys Thr Leu Arg Glu
 50                  55                  60

Lys Met Lys Pro Phe Ser Trp Gly Met Ile Asn Gln Leu Asp Asn Cys
 65                  70                  75                  80

Ser His Leu Val Val Ile Leu Ala Lys Lys Asn Ala Arg Tyr Asp Ser
                 85                  90                  95

Pro Phe Phe Val Asp Val Met Ala Arg Lys Gly Leu Asn Ala Glu Gln
                100                 105                 110

Gln Gln Ala Ala Leu Thr Lys Tyr Lys Ala Leu Gln Glu Glu Asp Met
            115                 120                 125

Lys Leu Leu Glu Asn Asp Arg Thr Leu Phe Asp Trp Cys Ser Lys Gln
130                 135                 140

Thr Tyr Ile Ala Leu Ala Asn Met Leu Thr Gly Ala Ser Ala Leu Gly
145                 150                 155                 160

Ile Asp Ser Cys Pro Ile Glu Gly Phe His Tyr Asp Lys Met Asn Glu
                165                 170                 175

Cys Leu Ala Glu Glu Gly Leu Phe Asp Pro Gln Glu Tyr Ala Val Ser
                180                 185                 190

Val Ala Ala Thr Phe Gly Tyr Arg Ser Arg Asp Ile Ala Lys Lys Ser
            195                 200                 205

Arg Lys Gly Leu Asp Glu Val Val Lys Trp Val Gly
210                 215                 220

<210> SEQ ID NO 5
<211> LENGTH: 20
<212> TYPE: PRT
<213> ORGANISM: Haemophilus influenzae

<400> SEQUENCE: 5

Lys Thr Leu Arg Glu Lys Met Lys Pro Phe Ser Trp Gly Met Ile Asn
 1               5                  10                  15

Gln Leu Asp Asn
             20

<210> SEQ ID NO 6
<211> LENGTH: 49
<212> TYPE: PRT
<213> ORGANISM: Haemophilus influenzae

<400> SEQUENCE: 6

Lys Lys Asn Ala Arg Tyr Asp Ser Pro Phe Phe Val Asp Val Met Ala
 1               5                  10                  15

Arg Lys Gly Leu Asn Ala Glu Gln Gln Gln Ala Ala Leu Thr Lys Tyr
             20                  25                  30

Lys Ala Leu Gln Glu Glu Asp Met Lys Leu Leu Glu Asn Asp Arg Thr
         35                  40                  45

Leu

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
actcatatga ctcaacttac tcgtgaa                                        27
```

-continued

```
<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
actaagcttc cccacccatt tcaccacttc a                              31

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gctcaacagc gtattacgac cc                                        22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gggtcgtaat acgctgttga gc                                        22
```